United States Patent
Laird et al.

(10) Patent No.: US 7,221,928 B2
(45) Date of Patent: May 22, 2007

(54) MOBILE EMERGENCY NOTIFICATION SYSTEM

(76) Inventors: Mark D. Laird, 21 Ferguson St., Milford, MA (US) 01757; Michael Glier, 74 Southwest Ave., Jamestown, RI (US) 02835

(*) Notice: Subject to any disclaimer, the term of this patent is extended or adjusted under 35 U.S.C. 154(b) by 166 days.

(21) Appl. No.: 10/957,083

(22) Filed: Oct. 1, 2004

(65) Prior Publication Data

US 2005/0085257 A1 Apr. 21, 2005

Related U.S. Application Data

(60) Provisional application No. 60/507,839, filed on Oct. 1, 2003.

(51) Int. Cl.
*H04M 11/04* (2006.01)
(52) U.S. Cl. .............................. 455/404.1; 455/404.2; 379/39; 340/825
(58) Field of Classification Search ............. 455/404.1, 455/404.2, 11.1, 552.1; 342/386; 340/539.11, 340/825, 573; 379/39; 348/39
See application file for complete search history.

(56) References Cited

U.S. PATENT DOCUMENTS

| | | | |
|---|---|---|---|
| 6,459,965 B1 | 10/2002 | Polivka et al. | |
| 6,526,350 B2 | 2/2003 | Sekiyama | |
| 6,677,894 B2 | 1/2004 | Sheynblat et al. | |
| 6,707,421 B1 | 3/2004 | Drury et al. | |
| 6,992,580 B2* | 1/2006 | Kotzin et al. | 340/539.11 |
| 2003/0174090 A1* | 9/2003 | Spilker et al. | 342/386 |
| 2004/0005861 A1* | 1/2004 | Tauchi | 455/11.1 |
| 2004/0133668 A1 | 7/2004 | Nicholas, III | |
| 2004/0199056 A1* | 10/2004 | Husemann et al. | 600/300 |
| 2004/0204032 A1* | 10/2004 | Hisano et al. | 455/552.1 |
| 2005/0153680 A1* | 7/2005 | Yoshioka et al. | 455/404.1 |

\* cited by examiner

*Primary Examiner*—Joseph Feild
*Assistant Examiner*—Phuoc Doan
(74) *Attorney, Agent, or Firm*—Weingarten, Schurgin, Gagnebin & Lebovici LLP

(57) ABSTRACT

A handset uses one or more systems, such as GPS, a carrier-based network or a wireless local area network, to ascertain its location. The handset can include sensors, such as temperature or heart rate sensors. In response to detecting an attempt to place an emergency call or send a message, or in response to automatically detecting an emergency, the handset provides a server with the identity and location of the handset and information about the emergency. The server provides the handset with information to correct errors in the location information or the server corrects the location errors. Communications between the server and handset are carried over the carrier-based network, WLAN and/or another wireless channel. The server displays information about the handset, a user and the sensors, so a dispatcher can dispatch assistance and/or provide information about the emergency to another agency.

43 Claims, 8 Drawing Sheets

MOBILE EMERGENCY NOTIFICATION SYSTEM

CROSS REFERENCE TO RELATED APPLICATIONS

This application claims the benefit of U.S. Provisional Application No. 60/507,839 titled "Campus Security System," filed Oct. 1, 2003.

STATEMENT REGARDING FEDERALLY SPONSORED RESEARCH OR DEVELOPMENT (Not applicable).

BACKGROUND OF THE INVENTION

The present invention relates to systems that report potential emergency situations, including emergency telephone call (911) systems and, more particularly, to systems that provide secondary notifications of emergency calls to third parties.

Emergency operators can efficiently dispatch appropriate first responders, such as emergency medical technicians (EMTs), police officers or firefighters, as a result of emergency calls. However, when an emergency call is placed by a person who is located on an institutional campus, the campus's safety organization is typically not notified of the emergency until after the first responders are dispatched or reach the site of the emergency. Often, the campus safety organization is never notified. This is unfortunate, inasmuch as the campus safety organization is usually well positioned to quickly respond to an emergency and may be able to reach the site of the emergency before the first responders. Moreover, the campus safety organization typically has current and detailed knowledge of the campus's (sometimes frequently changing) geography, buildings and other infrastructure, and this information can help the first responders more expeditiously reach the site of the emergency or render assistance once they arrive.

Even if a campus's safety organization were notified of an emergency, the campus safety organization cannot establish voice communication with the caller who placed the emergency call, because no interference with emergency calls is permitted. Thus, the campus safety organization cannot gather any information about the emergency from the caller, even though such information might be useful in assisting with the current emergency or in preventing other emergencies.

Emergency calls are increasingly being placed from wireless telephones. Emergency operators are generally expert at dispatching appropriate emergency services, however when handling emergency calls from mobile telephones, the emergency operators sometimes must rely on callers to orally describe the locations of the emergencies. A mandate to automatically provide emergency operators with locations of mobile emergency callers precipitated installation of improved infrastructure, which removed some of the need for these oral descriptions. However, the accuracy of this automatically-provided location information is limited and varies depending on the type of system used to ascertain the location of the calling handset, atmospheric conditions, et cetera. Furthermore, the location information does not include vertical position information. Vertical position information can be very important, especially when emergency calls are placed from multi-story buildings, such as buildings on college or corporate campuses or in urban areas.

An emergency operator may require an oral description of the nature of an emergency, a victim's medical condition or history, a description of an assailant or other background information in order to properly respond to an emergency call. However, sometimes a caller's condition or situation renders the caller unable or unwilling to verbally provide this information. Under these circumstances, a proper assessment of the emergency may be delayed until the first responder arrives at the site of the emergency. Such a delay may preclude a favorable resolution of emergency.

Some campuses, urban areas and other areas are covered by wireless telephone systems that do not include emergency call systems. In these situations, no location information is automatically available when a caller calls a campus safety, police or other organization to report an emergency. The called organization must rely solely on oral descriptions from the caller regarding the nature and location of each emergency. However, as noted, sometimes the caller is unable or unwilling to provide this information.

BRIEF SUMMARY OF THE INVENTION

The invention provides methods and apparatus for providing secondary notifications to third parties, such as campus safety or security organizations, of indications of a potential emergency, including emergency calls. While emergency calls and mobile telephone handsets are used as examples, any indication of a potential emergency situation that can be detected by a handset, such as a mobile telephone, wireless PDA or wireless portable computer, may be used to trigger the notification system. A handset is configured to detect calls placed (or messages sent) to emergency services, such as calls to 911 in the US. When a handset detects such a call, the handset uses a secondary channel to send one or more messages to one or more preprogrammed destinations, such as to a campus security management system. Such a system displays a map of the campus and superimposes information about the handset and its user on the map, showing the location of the handset. An operator monitoring the display can dispatch campus safety or security personnel and/or contact the emergency service that originally received the call and provide additional information (such as vertical location information) to the emergency service.

The secondary channel can be a second voice channel, a data channel provided by the same communications carrier that provides the voice channel over which the emergency call is placed or another wireless data channel, such as one provided by a wireless local area network (WLAN). If the handset cannot communicate directly with the communications carrier or WLAN (for example, because the handset is in a "dead zone"), the handset sends the messages via other nearby handsets, which relay the messages.

The messages inform the campus security management system that an emergency call was placed. The messages include an identifier of the handset that placed the emergency call or an identity of the handset user and can optionally include additional information about the user, such as age, gender and medical conditions and sensitivities. The campus security management system optionally uses the handset identifier or user identity to access a database and fetch additional information about the user.

The handset also sends data to the campus security management system from sensors located in the handset or communicably coupled to the handset. These sensors can detect ambient temperature in the vicinity of the handset (for example to detect a fire), the handset user's pulse, a visual image within a field of view of one of the sensors or the state of a "panic" button, for example.

The handset also sends information to the campus security management system regarding the current location of the handset. This location information can be obtained from any available source, such as a global positioning system (GPS) receiver in the handset, wireless carrier telephone network location information (such as information based on which cell site(s) receive signals from the handset, time of arrival and/or angle of arrival of these signals) and/or location information gathered from communications between the handset and WLAN(s) in the vicinity of the handset.

This location information can be augmented or refined with additional information. For example, GPS information can be corrected with information from the Wide Area Augmentation System (WAAS) or other sources of navigation satellite data correction information, such as EGNOS and MSAT. Because satellite signals, such as WAAS signals, can be obstructed by tall buildings and thus are not always available in "urban canyons" and other locations, these signals can be received by roof-top receivers and rebroadcast to make them available to all handsets capable of receiving the rebroadcast. This rebroadcasting can be via radio signal, over the WLAN(s) and/or other wireless channels.

The source(s) of location information and correction information varies, as does the availability of wireless communication services, depending on the location of the handset, atmospheric conditions, etc. For example, wireless telephone, GPS and WAAS signals are more likely to be available when the handset is outdoors than when the handset is indoors, however WLAN signals are more likely to be available inside buildings than outdoors. Thus, handsets according to the present disclosure adapt, depending on which wireless service(s) is(are) available, and use the best available communication channel(s) and source(s) of location information. Consequently, the accuracy of the handset's location information can vary. The campus security management system display indicates the handset's calculated location and an uncertainty zone around that location, based on the accuracy of the calculated location.

BRIEF DESCRIPTION OF THE SEVERAL VIEWS OF THE DRAWINGS

These and other features, advantages, aspects and embodiments of the present invention will become more apparent to those skilled in the art from the following Detailed Description of the invention in conjunction with the accompanying drawings, in which.

DETAILED DESCRIPTION OF THE INVENTION

The contents of U.S. Provisional Application No. 60/507,839 titled "Campus Security System," filed Oct. 1, 2003 are incorporated by reference herein.

Figure 1:
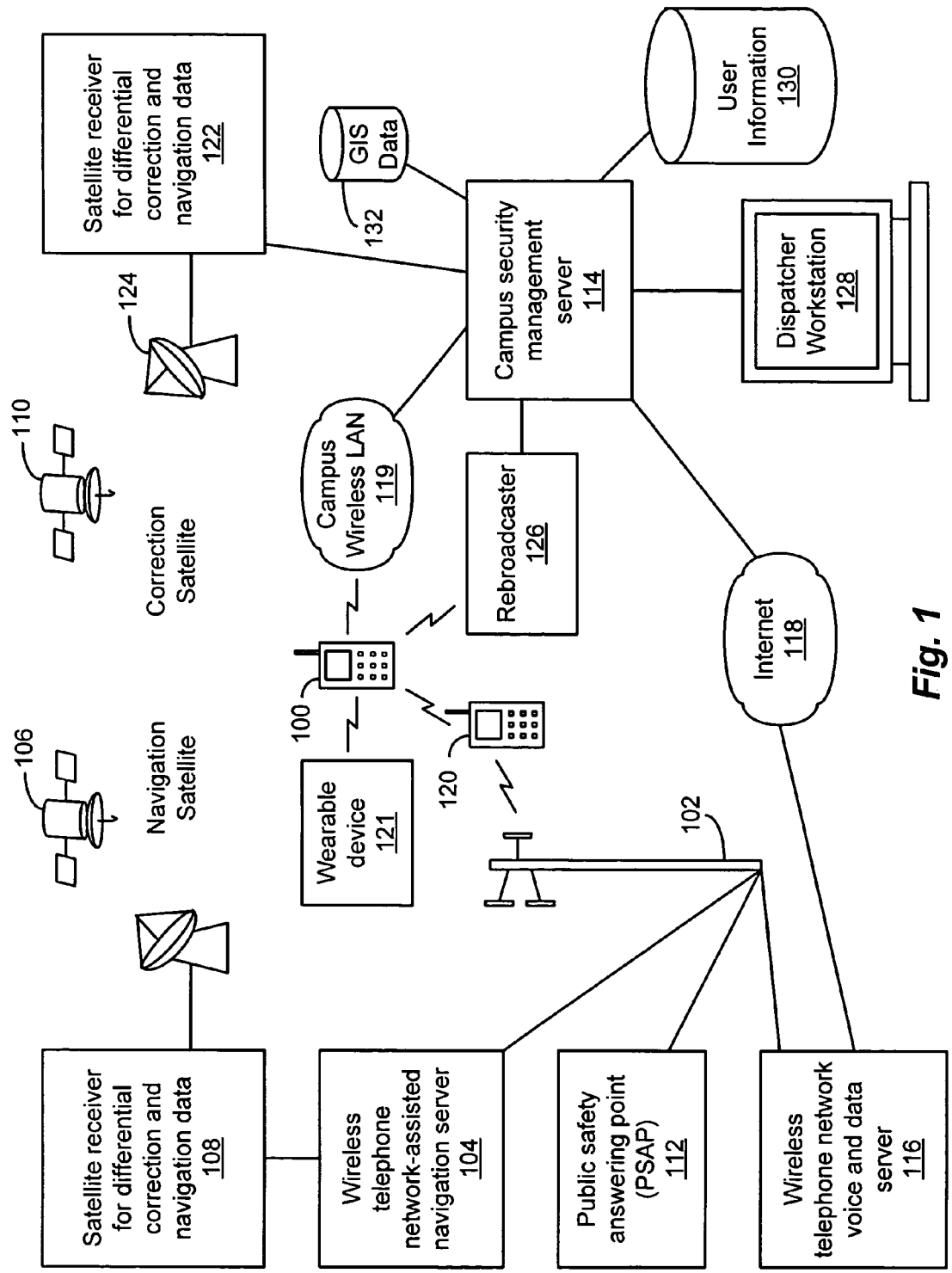
FIG. 1 is a block diagram of one embodiment of the present invention.

The invention provides methods and apparatus for providing secondary notifications to third parties of potential emergencies detected by wireless handsets. FIG. 1 is a block diagram of an exemplary system, according to the present disclosure. One or more wireless handsets, such as mobile telephones, wireless telecommunication systems for the deaf, wireless PDAs, two-way pagers or wireless portable computers, are served by one or more wireless networks. For example, an exemplary handset 100 is served by one or more wireless telephone networks (represented by cell tower 102).

The handset 100 and/or the wireless telephone network 102 can include a facility to ascertain the location of the handset. For example, the wireless telephone system 102 can include a network-assisted navigation server 104 to provide location information about the handset 100. The network-assisted navigation server 104 can use any of several well-known systems to ascertain the location of the handset 100. For example, the network-assisted navigation server 106 can use differences among times that signals from the handset 100 arrive at various cell towers to ascertain the location of the handset 100. Such a system is commonly known as "time difference of arrival." Another well-known network-assisted navigation system is called "angle of arrival."

Optionally or alternatively, the handset 100 includes a global positioning system (GPS) receiver (not shown) to receive signals from navigation satellites, such as satellite 106. Optionally, the network-assisted navigation server 104 is connected to a satellite receiver 108 for receiving differential correction and navigation data from satellites, such as satellites 104 and 110. The network-assisted navigation server 104 uses differential correction and navigation data from the receiver 108 to correct location information provided by the GPS receiver in the handset 100 and/or to provide the correction information to the handset to enable the GPS receiver to ascertain the location of the handset more quickly.

Emergency Call

If the handset 100 places an emergency call, the wireless telephone network 102 routes the call as dialed, such as to a public safety answering point (PSAP) 112. A user of the handset 100 can place the emergency call for any of a variety of reasons, including an actual emergency, such as an attack, threat, accident or health problem; a perceived emergency, including a sensation, communication, health concern, warning or other message or indication; or a perceived increased risk, including a sensation, indication or absence of an expected event, sensation, indication or communication.

If the call is placed to a PSAP 112, the wireless telephone network 102 provides the location of the handset to the PSAP in a well-known manner. An operator at the PSAP 112 evaluates the call and, if appropriate, dispatches one or more first responders. As noted, the precision of the location information provided by the wireless telephone network 102 varies, and the location information lacks vertical datum information. Thus, in prior art systems, the operator may be required to elicit additional location information from the caller.

Handset Detection of an Emergency Call

In systems according to the present disclosure, the handset 100 or the wireless telephone network 102 is configured to detect an indication of a potential emergency, such as an attempt to place an emergency call (or to send an emergency message) by the handset and to use a secondary channel to notify a campus security management system of the emergency indication (collectively hereinafter "call"). As used herein, "campus" refers to any predefined area, such as a college campus, amusement park, shopping mall or corporate campus. The area can be exclusively associated with the campus, such as an autonomous college campus. Alternatively, the campus can be co-extensive with unassociated areas. For example, a corporate campus can occupy portions of one or more floors of an office building, which also houses other, unassociated corporations.

An emergency call can be identified by its destination. For example, an emergency telephone call placed in the US or Canada generally has a dialed number of 911. Other countries or regions also have characteristic emergency dialed numbers, such as 999 (England), 112 (most of Europe) or 110 or 119 (Japan). Similarly, an emergency message, such as a short message service text message or an e-mail message, can be identified by its destination address, such as 4012723121@verizon.net or emergency@providence.ri.us.

Emergency calls are not, however, limited to voice calls and text messages. As used herein, "emergency call" includes all forms of communication that are attempted by the handset 100 in case of an emergency. Furthermore, other methods can be used to identify an emergency call. For example, a speech recognition system can be used to monitor a voice call for certain words that indicate an emergency situation. Text messages can be similarly monitored.

An application program in the handset 100 can detect emergency call attempts made by the handset by observing the destinations of call attempts by the handset and comparing these destinations to a list of one or more predetermined destinations. These predetermined destinations can include the emergency dialed numbers, text message destinations and e-mail destinations, as described above, as well as other destinations, such as a telephone number of a college campus security organization. The list of predetermined destinations can be entered via the handset's keypad or it can be downloaded from a central server.

The handset 100 can also detect emergency call attempts by other mechanisms, such as by detecting an activation of a "panic button" on the handset or a panic button activation on a wearable device 121 (discussed in more detail below), which is communicated to the handset by the wearable device. Other mechanisms for detecting emergency call attempts are described elsewhere. Furthermore, the handset 100 can be configured to detect emergencies and automatically attempt to place emergency calls and/or to notify a third party, as described below.

Figure 2:
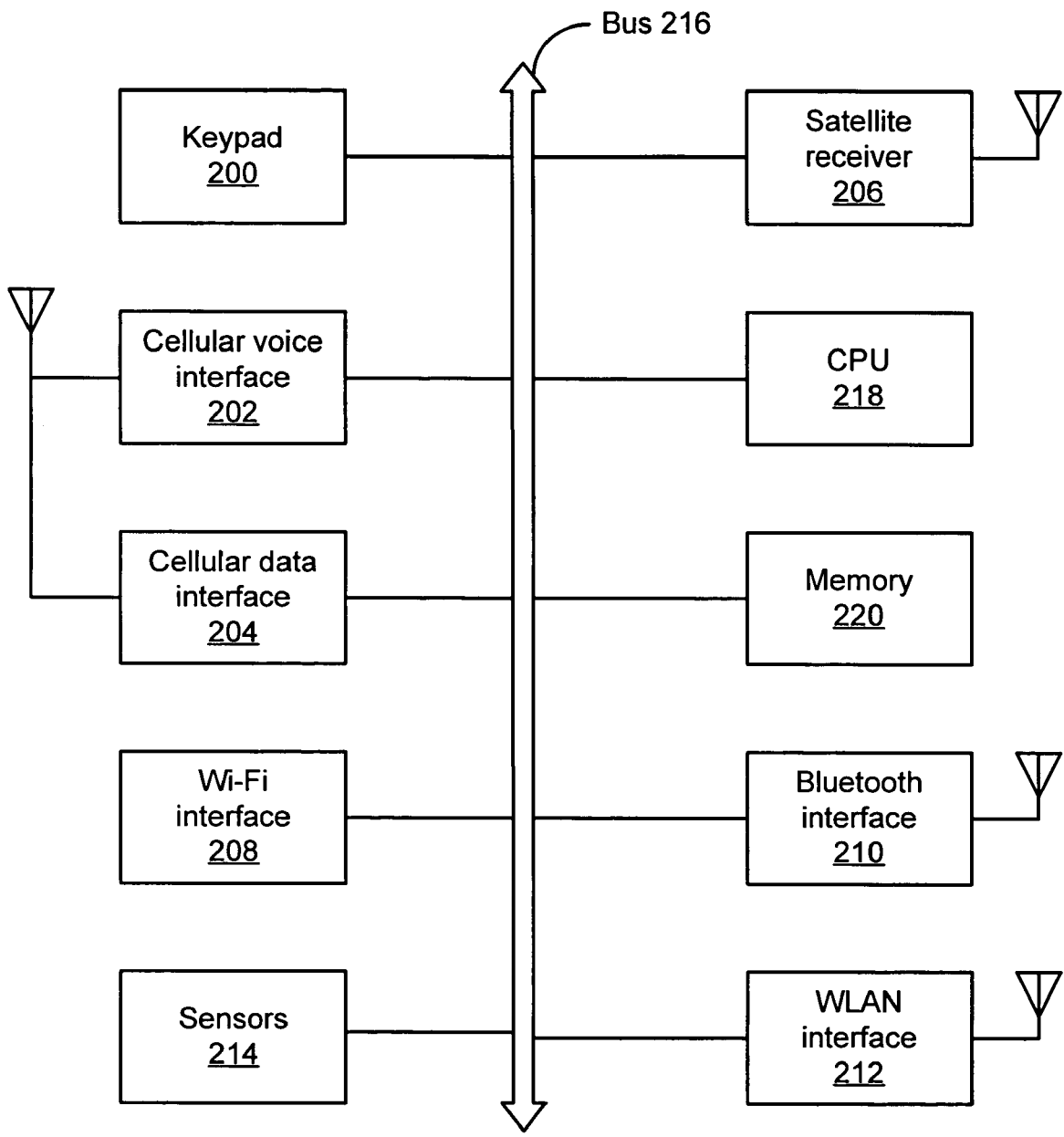
FIG. 2 is a block diagram of the mobile handset of FIG. 1.

FIG. 2 is a block diagram of a mobile telephone handset 100. The handset includes a keypad 200, by which a user can place a call or send a message. A cellular voice interface 202 modulates and receives radio frequency (RF) signals, enabling the handset 100 to place and receive voice calls over the carrier's wireless telephone network 102. A cellular data interface 204 modulates and receives RF signals, enabling the handset 100 to send and receive data via a high-speed data channel, as is commonly available through wireless protocols, such as the CDMA family of protocols and the GSM family of protocols.

Optionally, the handset 100 includes a satellite receiver 206 to receive location data from a navigation satellite. Although the present disclosure refers to the GPS satellite navigation system, other satellite or terrestrial navigation systems are acceptable. Examples of acceptable navigation systems include the Global Orbiting Navigation Satellite System (GLONASS), GALILEO and the Quasi-Zenith Satellite System (QZSS). In addition, the handset 100 can include a "software configured navigation receiver," which can be configured to receive signals from these and other sources of navigation information.

The handset 100 can also include a Wi-Fi interface 208 for connecting to available Wi-Fi "hot spots," a Bluetooth interface 210, a WLAN interface 212 and/or other wireless interfaces (not shown). Optionally, the handset 100 can include one or more sensors 214, as discussed in more detail below. These and other components of the handset 100 are interconnected by a bus 216.

A central processing unit (CPU) 218 executes software stored in a memory 220 to control operation of the handset 100. The software includes an operating system and an application program that performs the functions described herein.

Secondary Notification

Returning to FIG. 1, when the application program being executed by the CPU 218 of the handset 100 detects an emergency or an attempt to place an emergency call, the application program uses a secondary channel to send one or more messages to one or more preprogrammed destinations, such as a campus security management server 114, independent of the channel used to place the emergency call. The application program can detect the emergency call attempt by monitoring key presses on the keypad 200 or by acquiring call status information through telephony software running on the handset. Alternatively, the application program can register with the operating system of the handset 100 for notification of call attempts.

The messages sent by the handset 100 to the campus security management server 114 convey information about the handset, the user of the handset, the emergency, the attempted emergency call and/or other information, as described below. The handset 100 can use a (second) voice channel to send the messages. Alternatively, the handset 100 can send the messages over a data channel, via a wireless telephone network voice and data server 116, such as one maintained by the same telecommunications carrier that provides the wireless telephone system 102 or another carrier. Such a server 116 forwards the messages via a wide area network (WAN), such as the Internet 118, to the campus security management server 114. One or more of a carrier's data services or text messaging services, such as the short message service, can be used to carry the messages. Alternatively, the handset 100 can send the messages via a Wi-Fi connection (not shown), as is well-known in the art.

Alternatively, the handset 100 can send the messages via a campus wireless local area network (WLAN) 119, a Bluetooth connection (not shown) or any other wireless channel that is available to the handset. For example, the WLAN 119 can be an 802.11b or 802.11g wireless Ethernet network, and the handset 100 can be equipped with an appropriate wireless network transceiver.

If the handset 100 cannot directly access the wireless telephone system 102 or the WLAN 119, the handset can send the messages indirectly, via one or more other suitably configured handsets, such as handset 120. Communication between the handsets 100 and 120 can be via Bluetooth or other suitable wireless connection. This other handset(s) 120 relays the messages to the wireless telephone system 102 or the WLAN 119, such as by the mechanisms described above or by placing a call to the campus security management server 114 or a modem indirectly connected to the server.

Sensors

Optionally, sensors can be used in conjunction with the handset 100 to detect physical conditions in the vicinity of the handset. Data from the sensors can be used to automatically trigger an emergency call attempt and/or data from the sensors can be sent to the campus security management server 114. For example, an ambient temperature sensor can be used to detect fire, and a heart rate monitor can be used to monitor the health of the user of the handset 100. Threshold values, such as upper and lower temperatures, can be stored in the handset 100, either by downloading these values or entering them through the keypad 200. If a sensor value reaches its threshold, the application program being executed by the CPU 218 of the handset 100 can automatically place an emergency call and/or send a notification message to the campus security management server 114.

Some or all of the sensors can be included in the handset 100 (as described with reference to FIG. 2), in one or more units that are connected by wired or wireless links to the handset or a combination thereof. A wearable device 121 can include one or more biometric sensors and can be linked to the handset 100, such as via a Bluetooth or optical link. Biometric sensors can sense heart rate, blood pressure, body temperature, respiration rate, oxygen saturation, galvanic skin response, etc. Environmental sensors can sense temperature, smoke, oxygen level, noise, acceleration, toxins, radioactivity, etc.

WAAS Augmentation

Systems according to the present disclosure enable the location of the handset 100 to be ascertained with more precision than in conventional emergency call systems. Some systems use information received from WAAS to correct GPS data. The time required for a WAAS-enabled GPS receiver to achieve a first accurate position fix varies depending upon whether the GPS receiver contains current GPS and WAAS almanacs. These almanacs list the GPS and WAAS satellites. Modem WAAS-enabled GPS receivers have provisions to store a copy of the WAAS and GPS satellite almanacs. Typically, a standalone GPS receiver is initially loaded with a copy of the GPS almanac at the time of manufacture. However, the GPS almanac can become obsolete, due to changes in the constellation of GPS satellites. The WAAS almanac is usually not loaded at the time of manufacture, because the particular copy required depends on the location in which the receiver is ultimately used. To decrease the amount of time taken by a WAAS-enabled GPS receiver in a handset to ascertain the location of the handset, systems according to the present disclosure distribute the GPS and WAAS almanacs to handsets over higher bandwidth channels than are available directly from the satellites, as described below.

As with GPS signals, WAAS performance varies depending on the location and physical environment of a WAAS receiver. Because WAAS relay satellites (currently Inmarsat AOR-E & AOR-W) are in equatorial orbits, it is not always possible to receive signals from the satellites, such as when mountains, trees or large structures obstruct the view of the southern sky below certain azimuth angles. WAAS signals are not, for example, always available in urban areas bounded by tall buildings ("urban canyons"). However, WAAS correction data does not vary rapidly in time or across a region. Thus, WAAS data that is valid for a region can be shared with local handsets that are unable to receive their own WAAS signals directly from a satellite. Since institutional campuses are generally not free of obstructions, systems according to the present disclosure centrally receive and then rebroadcast WAAS data to handsets and provide this data to servers, such as the campus security management server 114.

A satellite receiver 122 for differential corrections and navigation data is connected to a receiving antenna 124 located on a rooftop, tower or other location with good reception from the satellites 106 and 110. The satellite antenna 124 and receiver 122 provides the correction and navigation data to the campus security management server 114 and, optionally, other campus security management servers (not shown). For example, other campus management servers within 75 air miles can be served by one antenna and receiver. The location of the antenna 124 is precisely known and is used as a reference for all local GPS or WAAS-enable GPS receivers in handsets used on the campus or in surrounding areas. Thus, the receiver can serve as a local area augmentation system (LAAS) for the handset 100.

Information from a WAAS satellite can be used to correct errors due to ionospheric delays, carrier frequency deviations, satellite wobble and the like. However, tropospheric delay characteristics vary by region and with time. A system of some fifty sampling stations distributed across the US collects data on tropospheric delays, averages this data and provides the average to the WAAS satellites for broadcast. Thus, correction data for tropospheric delays that is provided by the WAAS satellites is not specific to any particular region. However, region-specific tropospheric delay correction data is available from a number of sources, including the Continuously Operating Reference Station (CORS) system, the Internet-based Global Differential GPS (IGDG) system, FAA beacons operating at Category 3 airports and various private sources.

The campus security management server 114 uses WAAS correction data from the WAAS satellites 110 and/or from local CORS, IGDG or other sources. In addition, the campus security management server 114 receives region-specific tropospheric delay correction data from one or more of the sources mentioned above and/or the server calculates its own tropospheric delay corrections. The campus security management server 114 combines the region-specific tropospheric delay correction data with the other WAAS correction data and rebroadcasts this information to the handset 100, enabling the handset to more accurately ascertain its location. This rebroadcasting can be via the WLAN 119, via the Internet 118 and the wireless telephone network voice and data server 116 or via a Bluetooth connection (not shown) or a radio frequency (RF) rebroadcaster 126. The power of the rebroadcaster 126 and its antennas are configured and located so the rebroadcast signal reaches what would otherwise be dead spots on the campus.

The campus security management server 114 queries the satellite receiver 122 and collects and assembles reference data about each GPS satellite that is in view of the antenna 124. The campus security management server 114 obtains the WAAS and GPS almanacs that are appropriate for the WAAS and GPS grids in which the handset is located, and the server downloads these almanacs to the handset 100. The campus security management server 114 also collects WAAS correction data for all in-view GPS satellites and assembles and distributes a local WAAS correction data table for the in-view GPS satellites, as described above. Assembling and distributing WAAS correction data for only in-view GPS satellites minimizes the size of the messages transmitted to each handset. Furthermore, providing WAAS and GPS data sets and almanacs to the handsets enables the GPS receivers in the handsets to operate in the more rapid starting modes described below. In some cases, the GPS receivers must receive these datasets before they can begin operating.

Handsets on a campus are considered local to their respective campus security management server 114, which means that each handset supported by the campus security management server 114 uses identical in-view WAAS and GPS satellites. The campus security management server 114 multicasts in-view satellite data and correction messages. These multicast messages can be sent as a UDP data stream via the data channel established by the handset 100 over the carrier network 102, via the WLAN 119, Bluetooth (not shown) or other wireless channel. Sending this data as multicast messages minimizes the requirement for the campus security management server 114 to provide real-time message responses to individual requests from handsets for essentially identical data. Only handsets that require this information join the multicast group(s) and receive the messages. Using multicast connections reduces the number of messages exchanged between the campus security management server 114 and the handset 100.

The campus security management server 114 employs different multicast groups to transmit updates at different intervals. Each handset 100 chooses to join one or more multicast groups, depending on the update rate required. This allows the handset 100 to elect to receive less frequent updates and reduce cost when infrequent updates are adequate to maintain precision and to elect more frequent updates when needed to maintain acceptable accuracy. For example, the handset 100 can choose to receive updates every five minutes under normal (i.e. non-emergency) circumstances and to receive updates every two seconds during an emergency (such as between the time an emergency call is attempted and the time the emergency ends).

The campus security management server 114 collects WAAS correction data with sufficient frequency to ensure that the latest data used by the server and distributed to the handset 100 deviate little from actual correction factors. Most correction factors change very slowly, so these updates need not occur frequently. However, if the campus security management server 114 detects a change in the correction data that would cause a change in location accuracy greater than about one-half meter, the server distributes a fresh update of the correction data. This parameter can, of course, be made adjustable. Otherwise, the periodic WAAS update rate is based on the needs of the active handsets. In one embodiment, absent the above-mentioned change in the correction data, the campus security management server 114 provides a WAAS update to the multicast stream once per minute.

If a handset 100 or the campus security management server 114 determines that the handset's position data is poor due to inadequate or low quality GPS data, a request is made for updated correction data or for an increased WAAS update rate. For example, the handset 100 can send a request to increase the WAAS update rate. Each such request results in cutting the update interval in half by providing updates halfway between existing periodic updates, using the next multicast group. A system configuration option sets the baseline and the minimum update interval. In one embodiment, the interval between updates is at least 15 seconds.

The campus security management server 114 transmits the correction data streams over all available channels, such as the WLAN 119, the rebroadcaster 126, Bluetooth and the Internet 118/wireless telephone network voice and data server 116. This allows the handset software to choose which data stream is most likely to provide the information that the handset needs in the least amount of time and/or at the lowest cost. If the handset 100 cannot receive the correction data from the campus security management server 114 via any channel, the handset reverts to receiving this information from the WAAS satellite 110.

One or more redundant campus security management servers and/or satellite receivers (not shown) can serve as backup stations for the campus security management server 114 and the satellite receiver 122, respectively. Similarly, the campus security management server 114 and/or the satellite receiver 122 can serve handsets (not shown) on other campuses, even if the other campuses are not in identical WAAS correction grid locations.

Alternatively, the campus security management server 114 receives uncorrected GPS data from the handset 100, and it receives correction data from the satellite receiver 122. When the handset 100 sends raw (uncorrected) GPS pseudorange data, the handset flags the data as being uncorrected and the handset identifies the GPS satellite(s) associated with the sent data. The campus security management server 114 calculates corrected location information from the raw GPS data and the correction data from the satellite receiver 122. Optionally, the campus security management server 114 provides this corrected location information back to the handset 100.

Although the present disclosure refers to WAAS location correction information, other sources of navigation correction information, such as the ground-based European Geostationary Navigation Overlay Service (EGNOS) are acceptable.

WLAN-Based Location Determination

Optionally or in addition, the campus security management server 114 ascertains the location of the handset 100 using information from the WLAN 119. For example, if the handset 100 detects that the number of available in-view GPS satellites has fallen below a number necessary to provide reliable location information, the handset uses WLAN-based location information, in addition to any available GPS data, to locate the handset. A geographical information system (GIS) database 132 contains information about the topology of the WLAN 119, locations of wireless access points in the WLAN and geographic regions covered by each of these access points. Such a GIS database can be created by surveying the campus, measuring signal strengths and generating test transmissions through the wireless access points.

Information about which wireless access point(s) in the WLAN 119 receives signals from the handset 100 and information from the GIS database 132 are used to ascertain the location of the handset. For example, if several wireless access points simultaneously receive signals from the handset 100, the handset is located within an intersection of the regions covered by the receiving access points. Other information from the WLAN 119 can be used to more finely resolve the location of the handset 100. For example, identifications of access point(s) receiving signals from the handset 100, strengths of the signals received by the wireless access point(s) and relative arrival times at the access points of these signals can be useful in this regard.

Optionally, routers that actively participate in the location process can be used. When a location request message is detected, the routers silence non-emergency traffic to reduce latency of the location messages. The handset 100 then sends messages encoded with sequence numbers, which the routers relay to each other to determine a relative time of flight. When the wireless access points are initially installed, distances among their antennas, and possibly cable lengths to the routers, are accurately determined, so the propagation times between them are known accurately. The routers can then synchronize their clocks, based on this known propagation time. Using synchronized routers permits time-stamping a message from the handset 100 by each router, thereby enabling calculation of a differential propagation time.

User Database

An optional database 130 stores information about the handset 100 and the user of the handset. For example, the database 130 can store contact information for the handset 100, such as the handset's telephone number, IP address and/or MAC address. If dynamic IP addresses are used, this information is updated in the database 130, when appropriate. The database 130 can also store information about capabilities and options settings of the handset 100 and a log of interactions or incidents involving the handset. Some handsets exhibit different capabilities or interactions when the handsets are docked to base stations. The database 130 can include information about these variations and information about the current state of the handset 100.

The database 130 can also store the user's name, physical description, photograph, affiliation with the campus (e.g. student, faculty, staff or visitor), medical history, medical condition, drug allergies, home address and telephone number, campus address and telephone number, doctor's contact information, a person to contact in case of emergency and other information that the user chose to disclose.

Messages from the handset 100 include an identifier of the sending handset or an identity of the user. This information is used to locate the user's record in the database 130. For example, the database 130 can contain records that associate handset identifiers with users. When the campus security management server 114 displays information about an emergency call attempt, the server can automatically display some or all of the information in the database 130 about the handset 100 and the user. Alternatively, the campus security management server 114 displays information from the database 130 in response to requests from the dispatcher.

Dispatcher Position Display

As noted, when the handset 100 detects an emergency or an attempt to place an emergency call, the handset sends messages to one or more predetermined destinations. These messages can be sent sequentially or in parallel. The destination(s) can be selected based on information available at the time of the emergency or call attempt or on information that subsequently becomes available, either locally or as a result of communications sent to the handset. Thus, some destinations can be notified of the emergency somewhat later than the original detection. Local information (on which the destination selection is based) can include data from the sensors. Local information can also include results from computation, including algorithms that process the sensor data or that detect indications or derive indications, such as timeouts, errors, absences of desired responses, inappropriate responses, actions or inactions by the user of the handset 100. Communications to the handset 100 can be from a target of a prior communication or attempted communication, a solicited response from another site or an unsolicited message, such as a warning message.

When the campus security management server 114 (or another such server (not shown)) receives a message from the handset 100 indicating that the user or the handset attempted to place an emergency call, the server obtains location information about the handset. Depending on the wireless network, the handset's capabilities and other factors, the location information can be corrected or uncorrected location information. In addition, the (uncorrected) location information that the handset provided (or would have provided) to the PSAP 112 is also sent by the handset to the campus security management server 114.

Figure 3:
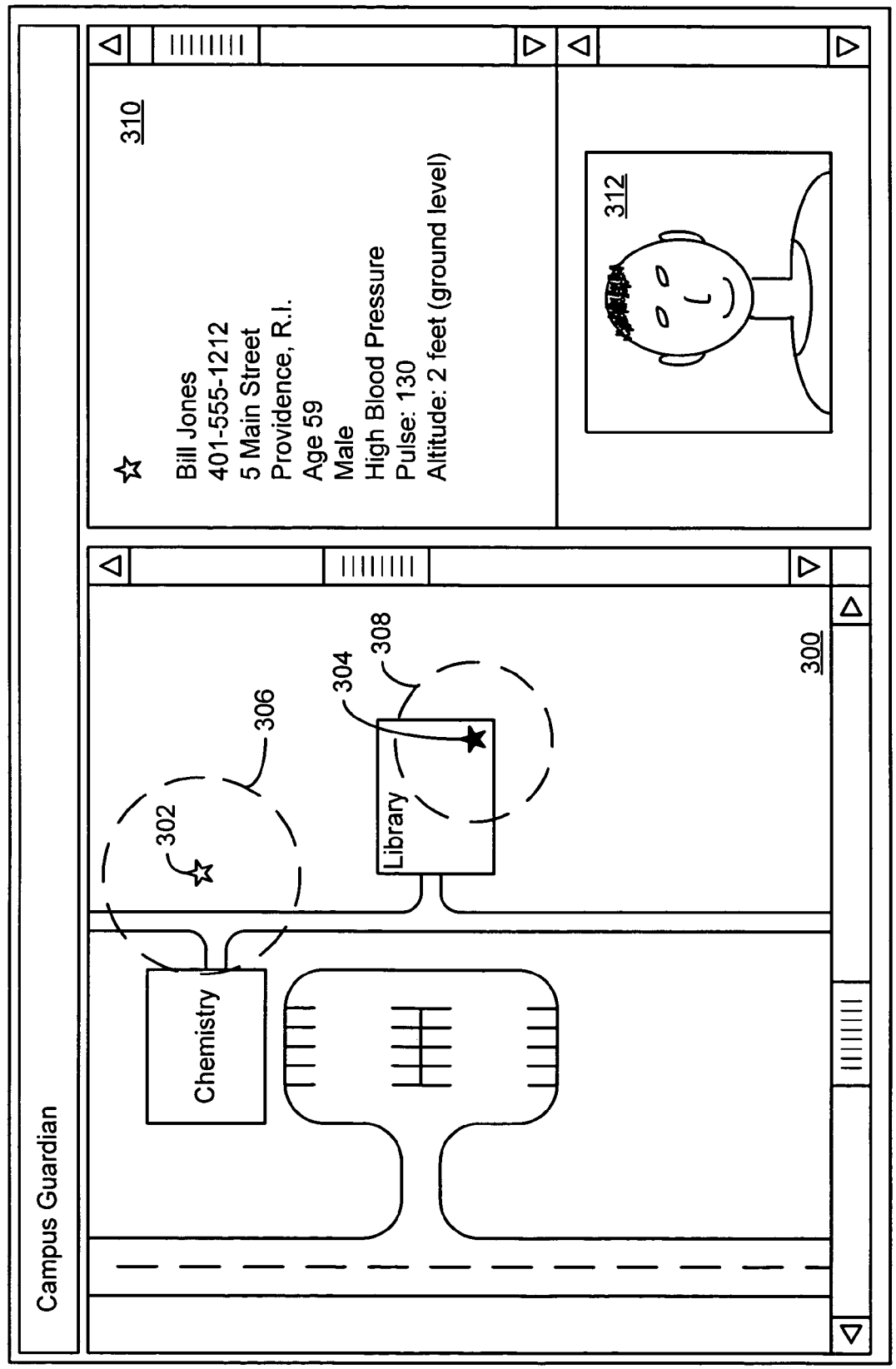
FIG. 3 is an exemplary display shown on the dispatcher workstation of FIG. 1.

The campus security management server 114 displays information about the emergency on a dispatcher workstation 128. An exemplary display is shown in FIG. 3. The displayed information can include a map 300 of the campus. Information about the handset and its user can be displayed as icons superimposed on the map 300 to represent the corrected location 302 and the location 304 that was provided to the PSAP. Uncertainty in the locations can also be represented by outlines 306 and 308. Information about the user, the handset and data from the sensors can be displayed as text 310. In addition, an image 312 of the user can be displayed. An operator monitoring the dispatcher workstation 122 (FIG. 1) can dispatch campus safety or security personnel to the site of the emergency. Furthermore, the operator can place a call to the PSAP 112 and provide additional information about the emergency, such as its vertical position. Alternatively, the operator can be prepared to receive a call from the PSAP 112 soliciting additional information about the emergency.

The secondary notification to the campus security management server 114 includes information about the originally-attempted emergency call, such as the destination number or address, the time of the attempt, whether the attempt was successful, whether the contact is still active or when the call ended or how the call ended (for example, loss of signal, ended by the caller or the telephone network, ended by the PSAP 112 or due to incomplete data). If the attempted emergency call failed, this secondary notification provides a means of notifying a secondary service, such as a campus security management organization, that the call was attempted, as well as providing the secondary service with all the intended contact information, so the secondary service can attempt to establish communication, directly or indirectly, with the originally-intended contact.

The campus security management server 114 correlates multiple emergency calls using spatial and temporal similarity in order to report and display them as a group. This format makes it possible to easily filter duplicate reports and use multiple reports to assist in localizing the emergency.

Degraded Modes of Operation

Systems according to the present disclosure have the ability to use some or all of the available location data, including WAAS, GPS and WLAN-based data, to achieve the most precise possible automated determination of the location of a handset. The simplest method or combination of methods is used to compute an accurate position in the shortest possible time. Degraded modes are also supported, including using GPS alone (when a WAAS signal is not accessible), providing available GPS data (when the number of in-view GPS satellites is not sufficient or the satellites are incorrectly positioned for an accurate location determination) and using WLAN data (when GPS data is unavailable or inadequate). As noted, all location information, even corrected location information, has some inherent uncertainty. Information provided to the dispatcher via the dispatcher workstation 128 reflects the extent of this uncertainty, which, when overlaid on a map, assists the dispatchers and responders in determining an optimal search approach.

If a handset 100 detects a degradation or loss of its local WAAS correction signal from the satellites 110 and from the campus security management server 114, the handset begins to utilize the last known WAAS correction data according to one of multiple strategies. Each strategy relies on historic data and includes computations based on the approximate location of the handset, current solar cycle, time of day, time of year and the local history of the rate of change of the WAAS correction signals. The handset 100 can compute estimated future values of the WAAS correction data, based on the historical data and the local rate of change. The handset 100 uses the last known signal data to calculate these estimated future values and, thereby, to compute an estimated time at which the last valid WAAS data will result in a location fix error that would be greater than a position fix error using only in-view GPS satellites. If the handset does not receive WAAS correction data directly from a satellite at the expiration of this time, the handset sends a network request (pull) message to the campus security management server 114 to request updated GPS and WAAS correction data from the server. If the handset software detects a change in the handset receiver location that could potentially invalidate or negate the usefulness of the aged WAAS data, the handset ceases to use the correction data and computes position fixes using only information from in-view GPS satellites.

If the handset 100 detects an increase in geometric dilution of precision (GDOP) error (due to the loss of a sufficient number of widely-separated in-view GPS satellites), the handset increases the frequency of its requests to the campus security management server 114 to obtain updated WAAS correction data, especially satellite clock updates. The frequency of these requests is further increased if the handset 100 detects that both the rate and amount of change in each updated location fix exceed predetermined thresholds, i.e. the handset detects changes in GDOP location faster or slower than the threshold. The initial threshold is set by the travel mode (e.g. walking, bicycling, riding in a vehicle, etc.) of the user. The rate of updates required is computed using one or more factors, which can include the capability of the handset 100, the user's recent travel history, a log of navigation satellite data, the user's current location, the current and predicted signal coverage, destination, and other current environment factors.

High Accuracy Position Determination

Use of GPS satellites to determine position has become widespread. However, a GPS position determination has inaccuracies due to errors that cannot be corrected by a simple GPS receiver. These errors are unique to each satellite and can also vary over time and by location of the receiver.

The Federal Aviation Administration (FAA) developed and deployed a WAAS to provide continuous differential correction signals to WAAS-enabled GPS receivers, which significantly improves the accuracy and reliability of simple GPS position estimates for both aviation and non-aviation uses. WAAS signals are available throughout most of the continental US and use the same frequencies as GPS satellites, which allows a standard GPS receiver to detect and process the WAAS signals.

WAAS satellites send augmentation messages with clock corrections, ephemeris corrections and ionospheric corrections. Tropospheric error corrections cannot be made using WAAS, due to the localized nature of this error, so the tropospheric error data is removed from the data stream provided by the WAAS satellites. This allows a WAAS-enabled GPS receiver to apply its own tropospheric error correction, based on an atmospheric model based on the current location of the receiver.

A WAAS-enabled receiver processes WAAS augmentation messages as factors of position calculations. The GPS-like signal from a WAAS satellite can also be used by a WAAS-enabled GPS receiver as an additional source for calculating the receiver's position. The WAAS messages contain information that allows WAAS-enabled GPS receivers to correct errors in GPS signals, thereby providing a significant increase in location accuracy and reliability. The specified accuracy of WAAS is stated at 7.6 meters vertical and horizontal, however WAAS often provides accuracy of one to two meters horizontally and two to three meters vertically. Error data compiled by the National Satellite Test Bed (NSTB) division of the FAA has documented an average error of less than two meters horizontally and vertically over a three-month interval.

WAAS messages indicate which components of GPS are unusable due to satellite or other system errors or other effects. For example, WAAS sends a notification of a GPS satellite error within six minutes of the error.

As noted, modem WAAS-enabled GPS receivers have provisions to store a copy of WAAS and GPS satellite almanacs. The time required for a GPS receiver to achieve a first accurate position fix varies depending upon the starting mode of the GPS receiver. There are three possible starting modes.

If a GPS receiver has no valid copy of the GPS almanac, the receiver enters a "cold start" mode. The GPS almanac is a 15,000-bit block of coarse ephemeris and time model data for the entire GPS constellation of satellites. Without an almanac, the GPS receiver must conduct a very wide frequency search to acquire a satellite signal. Very often, signal acquisition takes several minutes to complete, because a large number of frequency cells must be searched. If the entire GPS constellation is searched, the procedure can take more than 12 minutes, because each GPS satellite transmits at only 50 bits per second (bps).

If the GPS receiver has a stored copy of a valid GPS almanac, the receiver enters a "warm start" mode, which greatly reduces the number of frequency cells that must be searched. The bulk of the time required to generate a position fix is the time required to acquire a 900-bit satellite data message (SDM) from each in-view GPS satellite. The SDMs are used to compute the GPS receiver's position. The SDMs are broadcast every 30 seconds at 50 bps. Assuming parallel operation of several GPS receiver channels, the average time required to obtain the SDMs from all the in-view satellites is approximately 30 seconds.

If the GPS receiver has a current, valid SDM from each in-view GPS satellite (a total of 7,200 bits for eight satellites), the receiver enters "hot start" mode. In this mode, the GPS receiver must receive range information from the satellite, which is not included in the SDMs. The time required to generate a position fix equals the time required to acquire a signal from each in-view satellite, plus the time required to generate a pseudorange measurement for each satellite. The total time is usually less than one second.

Loading the WAAS almanac can occur independently of loading the GPS almanac. Most GPS receivers include several channels, over which they can simultaneously receive signals from respective satellites. A GPS receiver can receive signals from a WAAS satellite over any of these channels. In any of the above-described modes, a WAAS-enabled GPS receiver can receive WAAS signals over one channel and receive GPS signals over other channels. Thus, the GPS receiver can load the WAAS almanac in parallel with receiving GPS satellite signals. Reception of a complete WAAS almanac from a satellite takes approximately five minutes.

Carrier Network-Based Location Determination

Some national carriers currently employ assisted GPS (A-GPS) to provide higher accuracy position fix information to PSAPs. A hybrid A-GPS is used in regions where GPS reception is poor or unreliable. The hybrid A-GPS uses cell tower location information to augment A-GPS location information.

During an emergency call, carriers that support A-GPS correction data on their networks expect to interact with handsets according to a specific network protocol. One type of system uses the cellular network to provide A-GPS data messages to the handset, which then returns time-stamped, raw pseudorange measurements to the network, and a network element computes the handset location. Another type of system provides detailed GPS constellation data and timing signal hints to the handset, which then computes its location and reports its location back to the network. While this high-level protocol can vary from carrier to carrier, the contents of the A-GPS data messages that are sent by the network to the handset are similar from carrier to carrier. The handset responses are also similar from carrier to carrier.

Because a handset can receive WAAS data from satellites, the handset can compute a more accurate location fix than by using only A-GPS information. However, large differences in location fix accuracies can occur if a carrier network GPS support server (such as the network-assisted navigation server 104 shown in FIG. 1) uses an atmospheric delay model that is not appropriate for the current location of the handset. Location fix errors are largely attributable to errors caused by inappropriate compensations for ionospheric delays. Additionally, the carrier network GPS support server typically does not have local tropospheric delay correction data for the current location of the handset. The carrier network GPS support server usually zeros out this component of the computation. Other delays are caused by latency in the carrier network, which may delay delivery of current satellite clock updates between the carrier network GPS support server and the handset.

As noted, existing systems for providing handset location information to PSAPs have significant shortcomings. For example, existing systems do not provide vertical position fix data from the handset. Current emergency communications protocols do not provide a means of reporting vertical position information. WAAS-enabled GPS receivers can ascertain their vertical location, often to within two to three meters. Such vertical position data can be very helpful in critical situations, such as when a caller is located within a multistory building. For example, using the callers vertical location, the caller's location could be isolated to within one or two floors. However, this vertical location information cannot be provided to PSAPs using existing systems. Furthermore, there is no guarantee that position correction data provided by a carrier's network is appropriate for the WAAS grid location of the handset.

Mobile Emergency Notification System Operation

Figure 4:
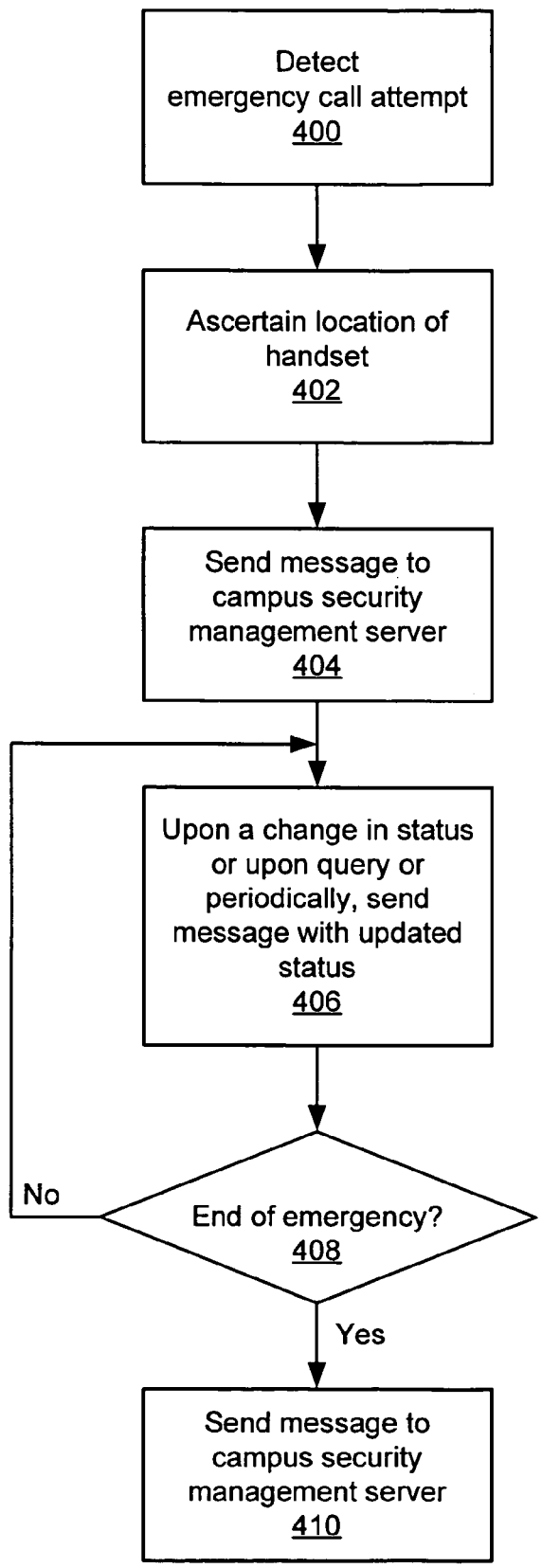
FIG. 4 is a flowchart illustrating operation of the handset of FIG. 1.

FIG. 4 is a flowchart illustrating operation of the application program stored in the memory 220, and executed by the CPU 218, of the handset 100. At 400, the handset detects an emergency call attempt. At 402, the handset ascertains its location. This can include using correction data provided by the campus security management server 114 to correct a GPS data received by the handset 100. Alternatively, as noted, the handset 100 can provide uncorrected GPS data to the campus security management server 114. At 404, the handset sends the location information, an identifier of the handset, the emergency number dialed and other information about emergency. The handset 100 sends this information over the best available link. For example, if the campus WLAN 119 is available, the handset uses this channel.

At 406, the handset 100 sends subsequent messages with updated status information about the emergency. The handset 100 can send these update messages periodically, in response to queries from the campus security management server 114 and/or upon a change in the status of the handset. For example, if the sensor indicates a changed value or the emergency call is ended, the handset 100 sends an update message.

At 408, if the emergency is not ended, control passes back to 406. Otherwise, at 410, the handset 100 sends a message to the campus security management server 114 to indicate the emergency is ended.

Figure 5:
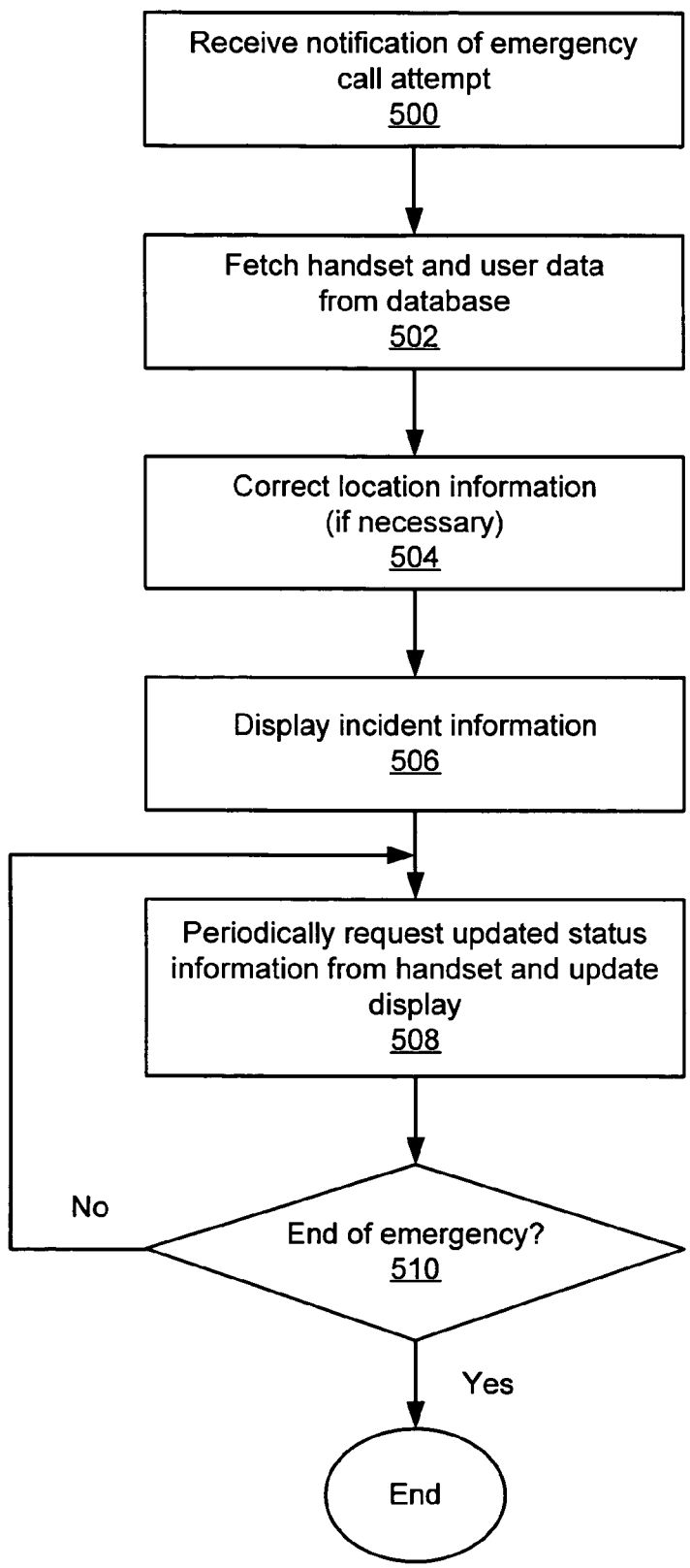
FIG. 5 is a flowchart illustrating operation of the campus security management server of FIG. 1.

FIG. 5 is a flowchart illustrating operation of the campus security management server 114. At 500, the server 114 receives a notification message from the handset 100 indicating an attempt to place an emergency call. The message identifies the handset 100 and/or the user. At 502, the campus security management server 114 uses the identification information provided by the handset 100 to fetch information about the handset and the user from the database 130. If the handset 100 provided raw location information (rather than corrected location information), at 504 the campus security management server 114 corrects the raw location information using correction information provided by the satellite receiver 122. At 506, the campus security management server 114 displays information about the incident on the dispatcher workstation 128. The dispatcher can interact with the campus security management server 114 via the workstation 128 to request additional information or reformat the display.

At 508, the campus security management server 114 periodically requests updated status information from the handset 100. Responses from the handset 100 to these requests provide updated location information about the handset, as well as updated sensor data. Thus, the dispatcher can monitor the emergency situation in real time. The frequency of these update requests can depend on the nature of the emergency. For example, if sensor data indicates a medical emergency, these updates can be as frequent as once per second. Alternatively, the dispatcher can specify the update frequency through the dispatcher workstation 128. At 510, if the emergency ends, the operation ends, otherwise control returns to 508.

For purposes of illustration, an aspect of the invention has been described in the context of providing notification (to a campus security management server) of an emergency 911 telephone call. However, the invention is applicable to any automatic location or automatic notification system. As noted, a system according to the invention can notify a central site in response to detecting an attempt to place an emergency calls, send a message, or other user action. An attempt to place an emergency call is not, however, necessary. Similarly, the system can notify the central site in response to an automatically detected situation (i.e. without a user action), such as a sensor detecting an excessive heart rate, radiation or an extreme temperature in the vicinity of the user. The system can, but need not, automatically place a call to an emergency service or other location. For purposes of this application, attempting to place an emergency call includes an explicit user attempt to place such a call or send a message or an automatic attempt to place a call or send a message (such as a result of detecting extraordinary sensor data or deviation from a planned route) by a handset or by a device communicably coupled to the handset.

Although the campus security management server 114 is shown as a single component, the server can comprise a number of interconnected servers, such as database servers, web servers, communication servers, mapping servers, navigation servers and the like. Similarly, although only one dispatcher workstation 128 is shown, systems according to the disclosure can include plural dispatcher workstations. Not all these workstations need to include identical interfaces and perform identical functions.

Wireless Virtual Escort System

The invention provides methods and apparatus for providing a wireless virtual campus escort to a user while the user proceeds from a starting point to a destination on the campus. The user interacts with the campus security management server 114 to request an escort and to select a route to the destination. The campus security management server 114 proposes one or more routes based, for example, on the user's current location, the desired destination, information stored in the GIS database 132 (such as locations of exiting walkways, roadways and lighting fixtures), current time of day, season, weather and expected arrival time. Optionally or alternatively, systems according to the disclosure track the locations and movements of users who are not necessarily proceeding to specific destinations, but whose movements are to be restricted or monitored.

As noted with respect to FIGS. 1 and 2, the handset 100 can include a GPS receiver or other facility, by which an application program executing within the handset can ascertain the location of the handset. Optionally, the application program also monitors sensors that are in the handset or that are communicably coupled to the handset. Alternatively, software executing within the campus security management server 114 ascertains the location of the handset and receives data from the sensors.

After the user selects a route, or restrictions are placed on the user, the campus security management server 114 uploads rules to the handset 100, and a software application executing in the handset thereafter monitors the location and movement of the handset and compares this information to the rules. The rules are constructed to detect actions, inactions and data from the sensors that are likely to indicate that an escorted user is in danger or a restricted user has or is about to perform an authorized action. For example, if an escorted user suddenly accelerates to a speed that is inconsistent with the user's mode of travel (for example, a walking user accelerates to a fifty miles per hour, indicating the user entered a vehicle), suddenly reverses direction, pauses (ceases making progress toward the destination) for more than a predetermined length of time or deviates from a prescribed route by more than a predetermined amount, or if a sensor indicates that a user sustained a strong blow, one or more of the rules "fire" and cause the system to treat the situation as a potential emergency (also referred to as an "alarm"). Similarly, one or more rules fire if a restricted user enters a restricted zone or comes within a predetermined distance of a restricted zone, or the restricted user leaves an authorized zone. If a rule fires, the handset solicits wellbeing status from the user or warns the user. If the user does not respond or return to the prescribed route or authorized zone, the handset 100 sends a message to the campus security management server 114.

In another embodiment, software executing in the campus security management server 114 monitors the location and movement of the handset and, in case of a deviation from a rule, attempts to contact the user through the handset.

If the campus security management server 114 is notified of, or detects, a potential emergency or unauthorized action, the server displays information about the user and the situation on the dispatcher workstation 128. As noted with respect to FIG. 3, the dispatcher workstation 128 can superimpose this information on a map of the campus. Optionally, the campus security management server 114 fetches additional information about the user from the user information database 130 and displays this information on the dispatcher workstation 128.

Wearable & Fixed Environmental Sensors

Optionally, sensors can be used in conjunction with the handset 100 to detect physical conditions in the vicinity of the handset. Data from the sensors can be used to automatically trigger an alarm and/or data from the sensors can be sent to the campus security management server 114. Some or all of the sensors can be included in the handset 100 (as described with reference to FIG. 2), in one or more units that are connected by wired or wireless links to the handset or a combination thereof. The connectable units can be carried by the user or they can be a fixed part of the campus infrastructure. For example, classroom buildings can be equipped with temperature, smoke and toxin sensors that can communicate via Bluetooth with any handset within range of the sensor. A wearable device 121 can include one or more biometric sensors and can be linked to the handset 100, such as via a Bluetooth or optical link. For example, the wearable device 121 can be in the form of a bracelet, necklace, wrist watch, lapel pin or other device. Optionally, the wearable device 121 can be inconspicuously carried by the user, such as in a pocket. The wearable device 121 can be inconspicuously sewn into the user's clothes.

Some sensors provide binary (yes/no) values, such as push buttons or smoke detectors. Other sensors provide continuous values, such as thermometers. (Digitized values are considered to be in a continuous range.) Yet other sensors process signals before providing them. For example, a speech recognizer processes utterances and provides a text transcription of the utterances. In another example, a voice stress analyzer analyzes sounds and provides an indication of the amount of stress the speaker is under.

Software handlers for the sensors can be loaded in the handset 100. These handlers include values, comparisons and actions. For example, a handler for a temperature sensor can include upper and lower threshold values. If the comparison yields a "true" result, the handler performs the specified action. For example, the upper threshold is compared with the temperature sensor's output, and if the temperature sensor's output is greater than the upper threshold, the handler signals an alarm.

Once attached to the user, some wearable devices can be detached only by a member of the security organization. For example, a bracelet can be attached to the user's wrist and locked in place. Such a bracelet cannot be easily removed without an appropriate key. Optionally, the wearable device includes sensors that detect attempts to surreptitiously remove the wearable device and notify the handset or the campus security management server 114 via any available wireless channel, including via other wireless devices. A user who is being attacked can trigger the alarm by removing or unclasping the wearable device without necessarily raising an attacker's suspicion. Such a wearable device would also trigger an alarm if an attacker removes the wearable device, such as jewelry or a chain, from the user.

Alternatively, the wearable device can be configured such that it can be removed without triggering an alarm only when the device is close to, and communicably coupled to, the handset and the handset is located at a predetermined location within the campus, such as a visitor center or security office. The wearable device can ascertain its location through the location-deter ning mechanism described above or by requiring that the handset be placed into a docking station or by providing alternative communications equipment at the facility that detects that the wearable device is present. The wearable device can communicate with the handset 100 using any available wireless channel, such as Bluetooth. Optionally, if the wearable device is separated from the handset 100, as detected by a loss of the wireless channel, the handset can raise an alarm. Upon loosing communication with the handset, the wearable device can enter a "beacon mode," as described in more detail below.

The campus security management server 114 can collect real-time data, such as snow accumulation, from properly equipped campus infrastructure. For example, a plow vehicle or operator can be equipped with a handset, and a sensor (communicably coupled to the handset) on the plow vehicle can detect whether the plow blade is in an upper or a lower position as the plow vehicle traverses walkways and roads. Based on the frequency with which the plow vehicle crosses a given point on the campus, the position of the blade when the vehicle crosses the point and the snowfall rate (which is generally available over the Internet from sources of weather information), the campus security management server 114 can estimate the amount of snow accumulated at the point. The snow accumulation amounts can be used to score various route segments during route selection and planning.

Due to conditions that are difficult to measure, such as drifting snow, the snow accumulation data should expire after a predetermined or calculated amount of time, similar to the way information about temporary obstructions expires. When available, the snowfall rate is factored into the aging to cause the snow accumulation data to expire sooner if the snowfall rate is high or the wind speed is high.

Rules can define a combination of sensor states that can be taken together to provide an indication of an actual emergency with more confidence than is available from the sensors individually. For example, a combination of an impact, a subsequent decrease in elevation, followed by a lack of motion can indicate a likely serious emergency situation.

Environmental sensors incorporated in the handset or communicating with the handset can be employed to warn of hazards, to report environmental hazards as part of alarm reports to assist in providing appropriate emergency assistance or to generate alarms independently. Heat/temperature, smoke, oxygen, toxin and radioactivity sensors are a few possible environmental sensors. Such sensors may be located on the campus and used to notify users within a defined radius of a potential hazard.

One condition is likely to be detected by sensors associated with multiple handsets. The campus security management server 114 correlates data from these multiple handsets in order to map an affected area. When a dangerous condition is detection, such as temperatures that indicate a possible fire, other nearby handsets can be identified and queried for sensor values relating to the condition. Using this data, it is possible to identify the safest routes, such as stairwells free of fire or smoke or the areas where toxins have the lowest concentration. Toxin propagation can be identified by updates over time in order to identify areas of risk. Users can be directed away from those areas, directed toward the safest escape routes and warning messages can be sent to users in the affected area. Additional information about the sensors and wearable device is provided above and below.

GIS Database

The GIS database 132 includes information that facilitates route planning. The GIS database 132 includes information about destinations and travel route segments. This information can include locations of building entrances, landmarks, meeting places, halls in buildings, outdoor walkways, driveways, open spaces (fields, etc.) and the like. For each of these items, the database can include information about nearby lighting fixtures and areas illuminated thereby (a "lighting map"), foliage, areas covered by surveillance cameras, buildings or other structures that might block satellite signals (a "shadow map"), grade (slope), known unsafe areas (including physical dangers, such as construction, icy walkways and slippery slopes above river banks), estimated travel times during various times of year or under various weather conditions, protection from the elements (such as roofs), hiding places (where perpetrators might hide) and proximity to manned security stations and emergency call boxes.

Social dangers, such as locations or areas that have been used or frequented by attackers or have been the subject of other crimes, such as burglaries or drug use, are treated separately using a crime map overlay of the campus service area, which is generated and maintained on the campus security management server 114. The crime map is created and updated from crime data collected by security management personnel and can include the type of crime, frequency of occurrence and locations or areas of occurrence. The data is evaluated and weighted by the system to establish the severity of a crime. For example, a bicycle theft would be evaluated as less severe than an assault. The crime map overlay is then used by the campus security management server 114 to evaluate the relative safety of computed or recommended travel routes. For example, if a serious a crime is reported on or near a particular location on a well-used night route that had previously been rated as "safe," the system presents an option to the system administrator to reclassify the route or area. Example classifications include "not recommended for females," "unsafe" and "do not use for routing." The system administrator can also maintain or restore a route or area to "safe" status. For example, after a perpetrator is caught or if a particular occurrence of a crime is considered not to warrant a change in route safety status.

In addition, information about the precision with which a path can be traveled or a person can be located within a space is helpful. For example, if a foot path is only three feet wide, a person that is positioned more than about three feet from the center of the foot path is likely to no longer be on the foot path and may have been taken off the foot path against his or her will. In contrast, a roadway can be tens of feet wide, so a person who is located within ten feet of the center of the roadway is still likely to be traveling along the roadway. Similarly, a person can be located anywhere within an outline of a quadrangle or a lobby. The GIS database 132 includes dimensions, such as widths, of travel paths.

The GIS database 132 maintains both current and predicted information about the quality of GPS signal coverage for the campus and along potential route segments. This information is used in selecting routes that have maximum signal coverage along their lengths and avoiding routes that have spotty or non-existent coverage or if the campus security management server 114 predicts GPS coverage will change while a user travels to a destination.

The GIS database 132 also includes information (a "signal map") about the quality of signal coverage for both voice and data channels provided by each of various wireless telephone carriers at various locations along potential routes. This information can be useful in selecting routes that have maximum signal coverage along their lengths and avoiding routes that have spotty or nonexistent coverage. One carrier might provide superior coverage along one route and a different carrier might provide superior coverage along a different route. Thus, information identifying a user's wireless telephone carrier is useful in selecting a route that has best coverage by that user's carrier. The user information database 130 includes an identification of each user's carrier. Similarly, information (a "WLAN signal map," "Bluetooth signal map," etc.) on the quality of coverage by the WLAN 119, Bluetooth channels, and other wireless networks is useful, as is information on whether the user's handset 100 includes capabilities to communicate with the WLAN, Bluetooth network, etc.

Initial information regarding GPS and each carrier's signal strength and coverage can be gathered by surveying the campus. Such a survey typically involves taking signal strength measurements at various locations on the campus and correlating these measurements with precise geographic location information about the sample sites. Additional real-time signal information can be obtained, and existing information can be refined, by polling handsets carried by security personnel and users as these people traverse the campus. The campus security management server 114 can poll these handsets for their locations and signal qualities detected by the handsets. Thus, the campus security management server 114 can constantly update both the GPS signal coverage and wireless network signal coverage information for all carriers serving the campus.

Optionally, one or more broadband cellular receivers (not shown) connected to the campus security management server 114 monitor wireless carrier frequencies to ascertain the operational status of all cell sites that are within range to service the campus. Information about cell site operational status is useful, because these cell sites or individual transmitters can cease operating without warning, thereby making that cell site or transmitter unavailable for exchanging information between the campus security management server 114 and the handset 100.

Other GIS database 132 information about locations and paths can include times (hours of the day, days of the week, vacation and holiday schedules, etc.) at which the locations and paths are likely to be crowded or desolate. Each item in the GIS database 132 has a rating, so a score for a proposed route can be calculated by summing the ratings of the items along the proposed route.

Route Selection & Planning

A user requests a virtual escort by interacting with the campus security management server 114 or with a human operator at the server. The user interacts with the server 114 via a web interface or via an application program executing in the handset 100. The server 114 can include a web server (not shown) to provide a web interface, and the user can request a virtual escort and select a route through a personal computer (PC) that is connected to the web interface, such as via the Internet. Alternatively, the application program in the handset 100 communicates with the campus security management server 114 over the WLAN 119, via Bluetooth or over the data channel provided by the wireless telephone network carrier 102. If the user interacts with a human operator, the human operator interacts with the campus security management server 114 via a network interface on the user's behalf.

In either case, the user specifies a destination location to the campus security management server 114 by selecting the destination from a menu or by typing the destination's name or other identifier on the keypad of the handset 100. The menu can be text-based or it can be graphical. The menu can contain fragments of maps of the campus, landmarks, coordinates, etc. A graphical selection mechanism can be displayed on a screen of the handset 100 by the application program executing within the handset.

Alternatively, the user specifies the destination by physically taking the handset 100 to the destination in advance of the escort request. For example, if the user anticipates requesting a virtual escort back to his or her dormitory or a parked vehicle after a concert, before leaving the dormitory or vehicle, the user can request the campus security management server 114 to ascertain the location of the handset and store this location in the GIS database 132 or in an "address book" in the user information database 130. Optionally, the user enters a name and a description of the location, and this name and description are used for subsequent menu-based beginning or destination selections.

When requesting an escort, the user's current location (i.e., the location of the beginning of the escort) can be automatically ascertained by the handset or the campus security management server 114, as described above. Alternatively, the user can identify his or her current location by selecting from a menu or typing the current location's name or other identifier on the keypad, as discussed above.

Once the user specifies the destination to the campus security management server 114, the server proposes at least one route from the user's current location to the destination. The security management server 114 consults the GIS database 132 to ascertain possible routes between the beginning and destination locations. The security management server 114 calculates scores for these possible routes, taking into account factors, such as the current time, estimated arrival time, weather, GPS signal conditions, the user's carrier's signal conditions, likelihood that foliage or other obstructions along the route will prevent satellite navigation or correction signals from reaching the handset 100, transient conditions (such as construction and road closures), major events (such as concerts) scheduled to end during the requested escort and number of other requests for virtual escorts at approximately the same time between proximate starting locations and proximate destinations. Optionally, the security management server 114 also uses real-time data, such as the condition of snow-plowed walkways, when calculating scores for the possible routes. (Collecting real-time data is discussed in more detail below.) Other considerations for selecting potential routes are listed in Table 1.

TABLE 1

Considerations for Selecting Potential Routes
Favored Routes May Place the User:

Where others are likely to be present, thus reducing
the risk of attack and increasing the
potential for assistance from others, if needed
Near scheduled patrols by security personnel
In areas of strong navigation and communication signals
On covered or plowed walkways in inclement weather
In areas of minimum risk of accidental danger or purposeful harm
In areas having surveillance cameras The security management server 114 presents the highest scoring routes, their distances, scores and estimated travel times, and the user selects one of the routes. Optionally, if the user does not select one of the proposed routes, the security management server 114 can present additional routes until the user selects one of the proposed routes.

Alternatively, the user can choose to specify a custom route, i.e. a route that is not proposed by the campus security management server 114. In this case, the user describes the route to the campus security management server 114 in one of several ways. The user can specify the route by specifying each turn along the route, or the user can travel the route in advance, with his or her wireless handset, and the server 114 or the handset 100 can record the locations of the handset. In yet another embodiment, the user specifies the custom route, intersection-by-intersection. In this case, the campus security management server 114 displays a list of nearby intersections, and the user chooses one of them as the starting point. The campus security management server 114 identifies all intersections that are adjacent to the specified intersection and displays a list. Again, the user chooses one as the next intersection, and the process repeats until the destination is reached.

These methods can be combined. For example, the user can specify a first portion of a route as a series of turns, and then the user can switch to intersection-by-intersection mode. Alternatively, the user can specify only a beginning part of the route, and leave the remainder of the route selection to later. The user can begin following the route before completing the route specification.

The user information database 130 stores information about previous routes traveled by the user. If the campus security management server 114 detects that the user frequently selects one or more routes, the server can offer to store these routes as "favorites" in the user information database 130. The campus security management server 114 can offer these routes instead of or in addition to routes calculated as described above. The user can select a favorite or other stored route in its entirety, modify the route or augment the route. In addition, historical actual travel times can be used to refine estimated travel times for route segments that this user previously traveled. If the campus security management server 114 receives information concerning a change in weather or other condition (such as construction) along a route that is currently being followed, the server sends an updated route to the handset 100 and notifies the user, such as with an alarm (ring tone, vibration, etc.).

Figure 6:
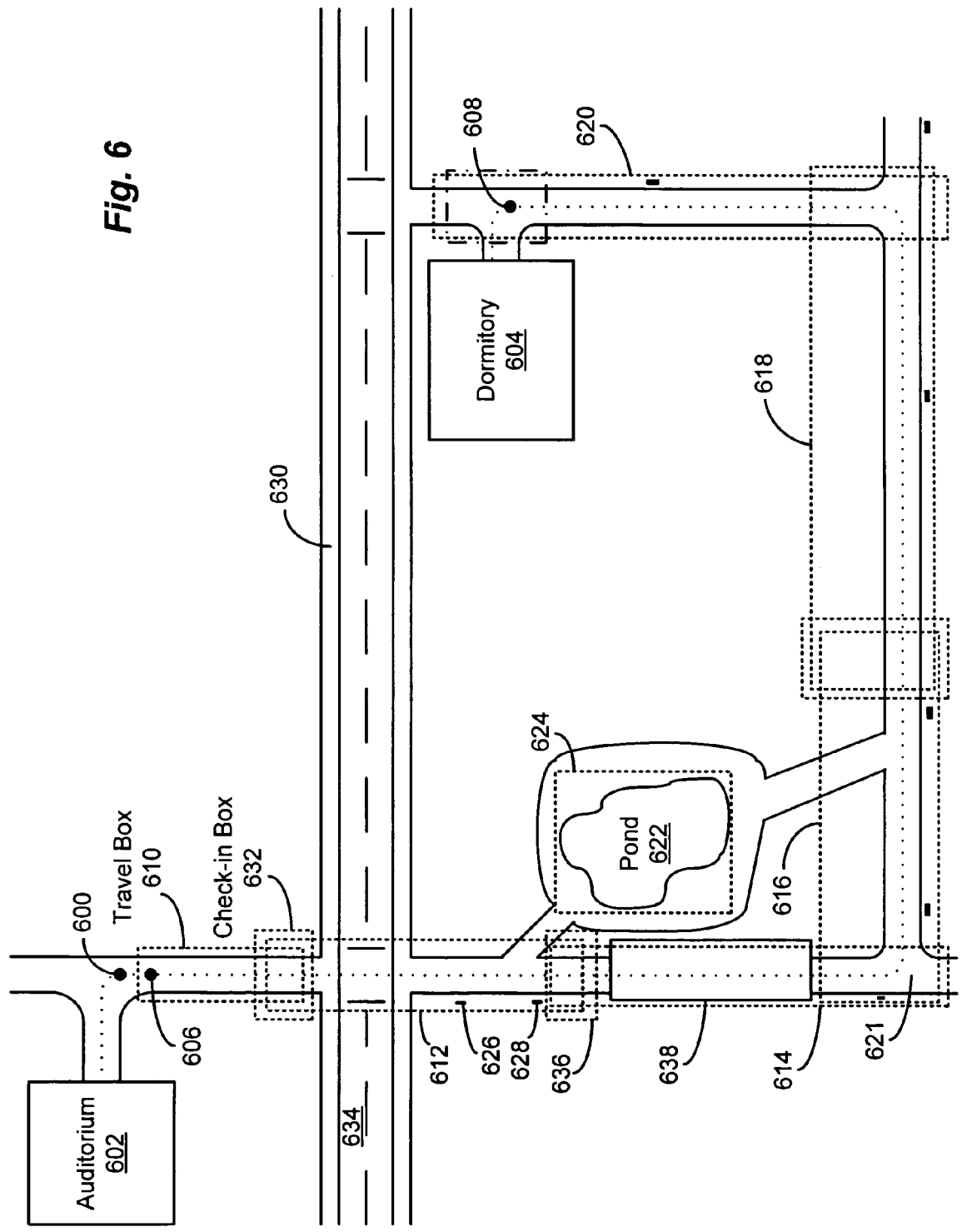
FIG. 6 is an exemplary map illustrating operation of a wireless virtual escort system, according to one embodiment of the present invention.

FIG. 6 illustrates an example scenario, in which a user requests a virtual escort after dark, along a route 600 from an auditorium 602 to a dormitory 604, starting at a starting point 606 and ending at an ending point 608. The route 600 was selected over other possible routes, because the walkways of the route are illuminated, such as by lights 626 and 628, as indicated in the GIS database 132. A different, shorter, route that includes sidewalk 630 is disfavored, because the sidewalk is not illuminated.

The campus security management server 114 uploads information about the selected route 600 to the handset 100. This information includes an identification of each turning point along the route 600, so the handset 100 can display this information to the user. Such a display can guide the user, for example with an instruction to "Turn left on Elm Street."

The campus security management server 114 also uploads rules for the selected route 600 to the handset 100. The rules define rectangular areas ("travel boxes") 610, 612, 614, 616, 618 and 620 in which the user is permitted to travel along the prescribed route 600. Each travel box covers one route segment. Multiple travel boxes can exist between turning points if an attribute, such as the width of the allowable region of travel, is wider in one section than in another section, the road or other way is curved or a long, straight region is broken into smaller sections in order to support detection of backtracking within a short time. Once the user leaves one travel box and enters a subsequent travel box, the handset 100 can delete the rules related to the previous travel box, because the user has made relatively constant forward progress from the starting point 606 to the ending point 608. However, to accommodate some backtracking by the user, adjacent travel boxes overlap one another. This overlap also ensures that the route is fully covered and monitored. In addition, the overlap accommodates some error in the ascertained locations of the handset 100. For example, due to location determination errors, in one sample of the handset's location, the location might be calculated to be closer to the starting point 606 than in an earlier location sample, even though the user moved away from the starting point.

Each travel box 610–620 covers a relatively straight route segment. Where the route 600 turns, such as at intersection 621, separate travel boxes 614 and 616 are used for each relatively straight route segment.

The rules can also define rectangular areas ("prohibited boxes") that the user is prohibited from entering. The user may not be permitted to enter a prohibited portion of the campus as a matter of policy. For example, a plumber working on a college campus might be prohibited from entering an electrical substation. Alternatively, the prohibited boxes can be used to identify dangerous areas, where the user is permitted to enter, but entry would be evidence of foul play or accident. For example, if the user fell or was pushed into a pond 622, the campus security management server 114 would appropriately notify the dispatcher. Thus, a prohibited box 624 surrounds the pond 622. Irregularly shaped prohibited areas can be covered by a plurality of overlapping rectangular prohibited boxes.

The campus security management server 114 also defines one or more rectangular "check-in boxes" along the route that the user is to follow. Each check-in box overlaps the end of a travel box. The check-in boxes are spaced apart, such that the user is expected to travel between each pair of successive check-in boxes in a relatively short period of time, such as 45 seconds. For example, a first check-in box 632 overlaps the end of the first travel box 610. In this example, the check-in box 632 is located less than 45 seconds (at the user's expected rate of travel) from the beginning of the travel box 610, because the user must cross a road 634 before proceeding, the user might have to wait for a pedestrian crossing signal before crossing the road and the estimated travel time along travel box 610, plus the estimated wait time at the pedestrian crossing, is longer than 45 seconds. Locations of the second and subsequent check-in boxes are calculated as the user traverses the route 600, as described below.

The actual distance between successive check-in boxes depends on the user's mode (and therefore expected speed) of travel. For example, a user walking on a sidewalk is expected to travel slower than a user riding on a bicycle or in a car, but faster than a user riding in a wheelchair. The actual distance between successive check-in boxes also depends on the check-in time interval. The locations of the check-in boxes can be selected such that no two successive check-in boxes are separated by more than (for example) 100 feet nor more than (for example) 45 seconds of travel time.

The location calculation can use other factors, such as the user's average speed over the recently traveled route segment(s), current weather conditions, terrain over the next route segment, expected quality of wireless network coverage in the next route segment (the signal map), expected visibility of satellites for location determination (the shadow map), and information about the user from the user information database 130, such as historic travel rates. For example, if a location that is otherwise acceptable for a check-in box, but the location has wireless network coverage or satellite reception that is expected to be poor, a location closer to the prior check-in location can be selected. For example, a covered walkway 638 might prevent the handset 100 from receiving GPS satellite signals. If a check-in box would otherwise fall within the covered walkway 638, the check-in box is moved closer to the beginning of the respective travel box. Thus, the second travel box 636 is placed before the covered walkway 638. The campus security management server 114 sends the calculated location (and time, as described below) of the next check-in box 636 to the handset 100.

Each check-in box has an associated due time window, which includes an expected travel time (such as 45 seconds) from the previous check-in message to the next check-in box, plus an allowance (such as 15 seconds) for the user to pause along the respective route segment and to accommodate variations in travel rate.

A conditional check-in mechanism can be employed at controlled intersections and other points of potential delays of known duration. If a delay above a threshold value occurs while in a check-in box having such a mechanism enabled, a second check-in is performed upon exit from the check-in box in order to adjust the expect time of arrival at the next check-in box.

For simplicity, the route 600, the travel boxes 610–620, the check-in boxes (such as check-in boxes 632 and 636) and the prohibited box 624 are all on one plane, however these elements can include an altitude component. For example, a travel box can allow a user to traverse halls or rooms of a multi-story building by specifying the altitude(s) of the floor(s) on which the user is allowed to travel.

Route planning for visitors is similar, except the routes may not have defined starting points and destinations. Visitors may be allowed to wander anywhere within the travel boxes, and the travel boxes can be large, to accommodate travel anywhere in a building or set of buildings, for example. In addition, the rules may allow a visitor to remain still, and check-in boxes need not be created for visitors.

Handset

Once rules are uploaded to the handset 100 and escorting begins, the handset begins monitoring the location and movement of the handset. The handset 100 maintains two logs in its memory 220. A current travel log is essentially a circular buffer that stores location and other information samples collected over a relatively short period of time, such as one minute. One or more samples can be taken during the time period represented by the current travel log. Each sample's information includes the time and date on which the sample is taken and the speed, height (altitude) and ending location of the handset at the end of the sample. The application program can apply the rules to the information in the current travel log to ascertain if a potential emergency condition exists and, if necessary, to send this information to the campus security management server 114.

A travel history log contains information similar to the current travel log, except the speed and height information are averaged over time intervals (such as five minutes) and the averages are stored. The travel history log contains information collected since the beginning of the current escort, i.e. since the user began following the current route. This information can be used for evidentiary purposes, such as to prove the user's whereabouts at particular times. To preserve the user's privacy, information in the travel history log is typically not provided to the campus security management server 114, unless an emergency situation exists. Information in a travel history log can be accessed by the user, such as to find the user's way back to a parked car. The application program executing in the handset 100 can, upon command from the user, accessed information in the travel history log and display this information on the screen of the handset.

The battery compartment of the handset can include a switch to detect if the compartment is opened or the batter is removed. If so, or if the handset 100 is turned off via its power switch, a small backup power source (such as a second battery or a capacitor) can keep the handset operating long enough to send a message to the campus security management server 114 and, thereby, raise an alarm. On a handset that employs a fuel cell, a shutdown procedure is followed before the fuel cell is turned off or removed. Initiating the fuel cell shutdown procedure can cause the handset 100 to send a message to the campus security management server 114.

The user can manually trigger an alarm by entering a predetermined sequence of keystrokes on the handset 100.

The sequence should not already being used by the handset for another function, so the available sequences vary by handset. For example, entering a two-digit code and pressing the "#" key can be programmed as the activation sequence. A different activation sequence can be configured for each user. If the handset is equipped with a speech-recognition capability, spoken words can be used to trigger an alarm. Alternatively, a loud noise can be used to trigger the alarm.

A handset 100 enters an alarm state because the user manually activated the alarm state, a rule in the handset fired or the campus security management server 114 commanded the handset to enter the alarm state. When an alarm is active, the handset 100 can collect identification information from nearby handsets and/or wearable devices, such as via Bluetooth communication. The handset 100 can report this information to the campus security management server 114 for storage in a log and to subsequently help identify potential witnesses.

The software application in the handset 100 can be configured such that if the handset enters an alarm state, the handset requests nearby handsets to actively monitor and report information to the campus security management server 114. The nearby handsets provide selected information, such as their locations and audio and/or images captured by the nearby handsets. This information provides the campus security management server 114 with additional opportunities to refine the location of the handset 100 that is in the alarm state. The campus security management server 114 can also gather additional information that may be useful in assessing the threat level and may help to identify the attacker and/or potential witnesses.

In addition, collecting environmental data from nearby handsets can help effect a rescue or direct a safe rescue or escape by identifying which areas present fewer risks. For example, knowing which of several stairwells has the lowest temperature or highest oxygen concentration could help direct people who are attempting to escape a fire. Similarly, knowing the areas of higher and lower toxin concentration provides data necessary to direct people away from areas of higher concentration.

If the user permits continuous location monitoring and the handset 100 has computed a location with reasonable accuracy (such as within one meter), the software in the handset can be configured to automatically mute or change the ringing mode of the handset to inaudible mode when the handset is in a classroom, theater or other venue where cell phone disruptions are prohibited.

Wireless Virtual Escort System Operation

The rules loaded into the handset 100 are constructed to detect situations that indicate that the user is lost, in danger, in fear, being attacked, ill or otherwise not making expected progress toward the destination. The rules can embody heuristics. For example, the rules can define permitted and prohibited locations (such as travel boxes 610–620) and movements of the user, as well as threshold values for sensor data. Table 2 lists exemplary rules. If the application program executing in the handset 100 detects the handset's movement (or lack of movement) or data from a sensor violates a rule, the application program notifies the user and inquires as to the user's well-being. The user must, within a predetermined amount of time, return to the prescribed route 600 and reply to the inquiry and indicate he or she does not need assistance. Otherwise, the handset 100 notifies the campus security management server 114, which declares an emergency and notifies a dispatcher via the dispatcher workstation 130.

TABLE 2

Exemplary Rules

Stopping for longer than a predetermined period of time. Thresholds periods can vary automatically based on data, including weather and GIS data, such as topography of a route segment. Longer thresholds may be used for locations adjacent crosswalks, elevators and door that requires a code, card or key. Sensors may detect the state of crosswalk signals to determine if a delay is warranted.
Sudden change in altitude, especially with a final position close to local ground level, may indicate a fall. A greater than normal allowance should, however, be made for vertical travel at a location known to have an elevator, without raising an alarm.
A sensor detecting an impact (acceleration), a loud noise, an elevated heart rate, a sudden change in galvanic skin response or any emergency condition described above.

To ensure the user makes progress toward the destination point 608, the campus security management server 114 establishes check-in boxes, as noted above, and estimates travel interval times between them. It transmits these locations and intervals to the handset 100 as part of the route information. When the handset 100 detects that it entered a check-in box, the handset notifies the campus security management server 114 by sending a message that includes the handset's location. Upon receiving this notification, the server 114 recalculates the check-in time for the subsequent check-in boxes. For example, after the campus security management server 114 receives a check-in message that indicates the handset entered check-in box 632, the server recalculates the check-in time for a second check-in box 636, based on the arrival time at the first check-in box 632, the user's average speed along the first route segment, i.e. through the first travel box 610. Thus, if the user arrives early at the first check-in box 632, the due time in the second check-in box 636 is made earlier.

On the other hand, if, based on the user's arrival time at the first check-in box 632, the user's speed along the first route segment, weather conditions, etc., the user is unlikely to be able to arrive at the second check-in box 636 within 45 seconds of arriving at the first check-in box 632, the campus security management server 114 recalculates the sizes and locations of the remaining travel boxes and check-in boxes.

If the campus security management server 114 does not receive a check-in message by the end of the due time window, the server declares the handset 100 to be late and can declare an alert or an emergency. However, the user might have reached the check-in box within the due time window, but the handset 100 might not have been able to send the check-in message due to a poor or nonexistent wireless network signal or network congestion. (Recall that the handset 100 can use any available wireless network, such as the wireless carrier network 102, campus WLAN 119, Bluetooth, etc., to send the check-in message.) Optionally, if the handset 100 is late, the campus security management server 114 repeatedly sends messages to the handset 100 to solicit the handset's location. If the handset responds and the travel status information provided by the handset 100 indicates that the user is traveling at a rate that would have placed the user in the missed check-in box(es) within the due time window(s), the server can treat the response as the (late/missed) check-in message(s). However, if the travel status information indicates that the user's travel rate is outside the predicted range, the server can declare an emergency.

Information about the expected quality of wireless service in each check-in box is stored in the GIS database 132. For example, no wireless signal might be expected while the user is on a covered walkway or in a tunnel 638. If wireless coverage is known to be unreliable in the area of a check-in box, the campus security management server 114 can forgo declaring an emergency as a result of a late (missed) check-in. The number of missed consecutive check-in messages that are permitted before the campus security management server 114 declares an emergency can depend on various factors, such as the quality of wireless service in the area(s) in which the handset is expected to be or a "dangerousness" rating (stored in the GIS database 132) for the route segment(s) involved. If wireless coverage is known to be poor, the campus security management server 114 allows more missed check-in messages than if the wireless coverage is known to be good.

Alternatively, several check-in boxes, more closely spaced than would otherwise be calculated, can be positioned along a route segment that is known to have poor wireless network coverage. Thus, the handset 100 has several opportunities to send check-in messages to the campus security management server 114.

Figure 7:
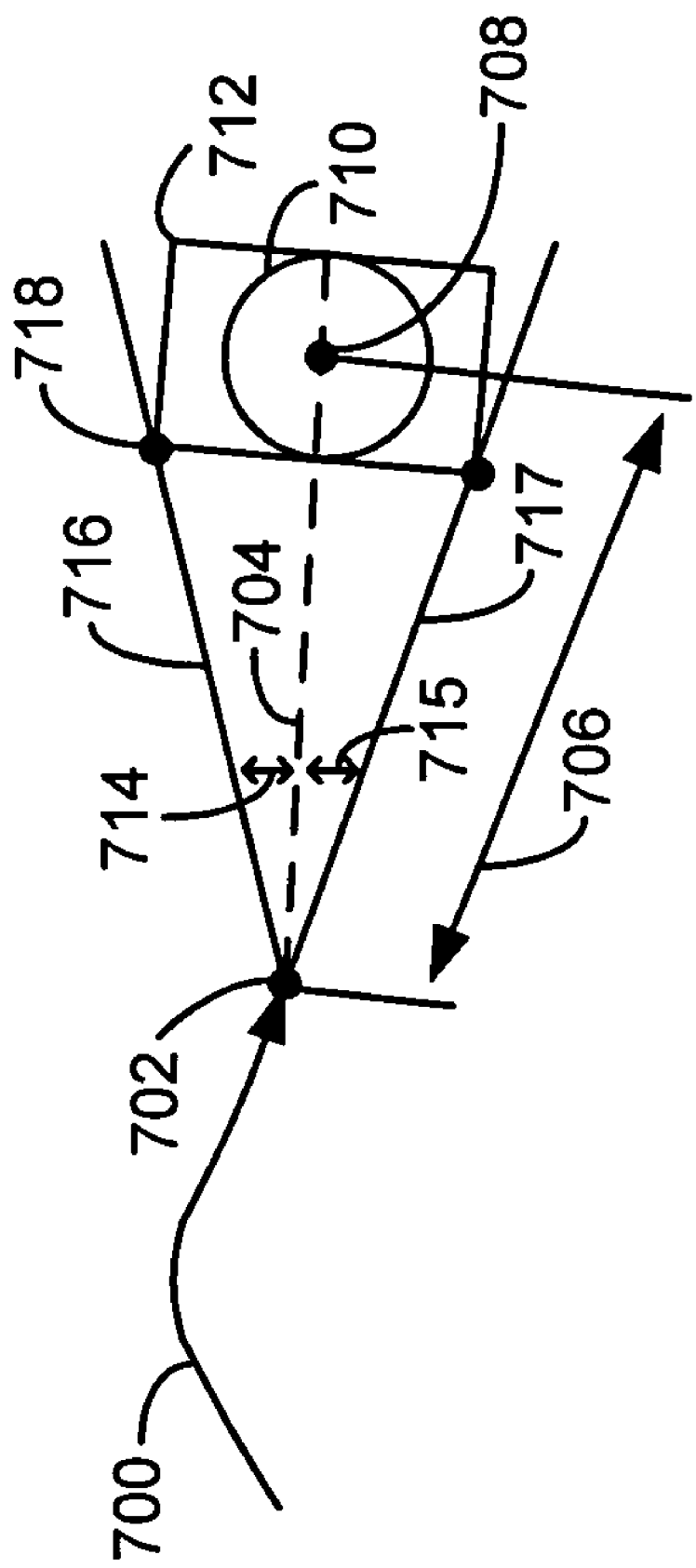
FIG. 7 is a diagram illustrating how a size and a position of a check-in box, such as one in FIG. 7, is calculated.

FIG. 7 illustrates an example of calculating the location and size of a next check-in box after a user enters a previous check-in box. Assume line 700 represents a user's actual path (not necessarily the user's prescribed route), and point 702 represents the user's location when the handset 100 sends a check-in message. If the user continues along a straight line 704 in the direction that the user is current heading for a distance 706, the user would reach a point 708. The distance 706 is calculated by multiplying the user's expected speed by the time interval of check-ins, such as 45 seconds. Thus, if the user continued along a straight line 704, in 45 seconds the user would be expected to reach point 708.

The handset's location can be determined to within an uncertainty amount that depends on the location determination method that is used, the number of satellites in view of the handset, etc. Circle 710 is centered on point 706 (the expected future position of the user) and has a radius equal to the uncertainty amount. Thus, if the user continued along straight line 704, in 45 seconds the handset would be expected to report its position as being within the circle 710.

The user may, however, deviate from a straight path. Lines 716 and 717 form 15 degree angles 714 and 715, respectively, with line 704. A next check-in box 712 is drawn, such that two of its sides are tangent to the circle 710, and two of its corners lie along lines 716 and 717, respectively. Such a check-in box 712 permits the user to wander within a 30 degree angle from the user's starting point 702.

The frequency of check-ins can be adjusted. For example, if a rule fires (and the rule indicates that the user is in danger) or an emergency is otherwise declared, the check-in interval can be reduced, such as to one second, so the dispatcher workstation 128 can display the handset's location in near-real-time. Examples of such situations include: the user's speed exceeds a threshold value (possibly indicating the user is running away from an attacker); the user suddenly changes direction (in a manner inconsistent with the prescribed route) by more than a predetermined amount, such as 15 degrees, after traveling at least a predetermined distance, such as 35 feet, in a previous direction (possibly indicating the user has been forced from the prescribed route or is trying to avoid an attacker); or the user stops (where a stop is unexpected) for more than a predetermined period of time, such as ten seconds (possibly indicating an encounter with an attacker). Similarly, if the emergency is ended, the check-in interval can be returned to normal or to an intermediate value to more closely monitor the user, in case of a subsequent incident. These limits are, however, programmable and can be adjusted.

If permitted to do so by the user's profile in the user information database 130, the user can discontinue an automated escort by entering a personal security code and a predetermined series of keystrokes on the keypad (a "discontinuance code") along with the user's personal security code. Alternatively, the handset 100 can be equipped to recognize the user's speech and respond to a user utterance to discontinue the escort.

Once the user reaches the destination point 608, a positive indication of safe arrival can be required, if so configured in the user's profile in the user information database 130. This indication can be a predetermined series of keystrokes or recognition of the user's voice uttering an appropriate command to the handset 100. If such an indication is not entered within a predetermined amount of time, the handset 100 raises an alarm by sending a message to the campus security management server 114.

Unless it is discontinued earlier or a positive indication of safe arrival is not required by settings in the user's profile, upon reaching the destination point 608, the escort service automatically ends and the handset 100 notifies the campus security management server 114. The handset 100 exchanges arrival confirmation messages with the campus security management server 114, which then closes the escort session in the handset. The server 114 logs the escort and may log escort details (such as the check-in locations), depending on the configuration of the system and the user permissions stored in the user information database 130. An indication, such as a text message or a sound, is generated on the handset 100 to notify the user that escorting has ended. In addition, if the user has reached the destination and wants to ensure that escorting is disabled, the user may enter a code to discontinue the escort.

Display

If an alarm is triggered, either manually or automatically, a map showing current position and recent historical position information related to the handset 100 is displayed on the dispatcher workstation 128 to assist a dispatcher in determining how to dispatch personnel. Time stamps associated with each handset location fix make it possible to determine if the user is still moving and assist the dispatcher in determining the best intercept point. Color codes and other attributes of markings on the dispatcher workstation 128 quickly convey information to the dispatcher. These include different colors for the positions before the alarm, at the time of the alarm and the current position. Color code and line type (solid, dashed, dotted, etc.) may be used to indicate deviations from an expected course, such as an escort session.

In general, the dispatcher workstation 128 does not display information about users who are not in an alarm state. This simplifies the display, so the dispatcher can concentrate on other duties or information related to alarms. However, the dispatcher can instruct the workstation 128 to display information about users who are not in an alarm state.

Color coding is used to convey information without cluttering the display. For example, orange, yellow and red can be used to identify the nature of an alarm, such as biometric data being beyond the threshold as opposed to the user who has simply lost his or her away.

The dispatcher workstation 128 can display information about a user, such as the most recent check-in time, whether the most recent check-in was late, whether a call to an emergency service (such as 911) is in progress, a reason why the user is an alarm state as well as user information (including phone number, address, name, description and photograph).

In addition to monitoring automatically escorted users, the campus security management server 114 can monitor a mobile security force to determine current locations (including altitudes) of force personnel and to quickly identify a member of the security force who is close to a handset when an alarm is raised for that handset. Upon request from the dispatcher, software that drives the dispatcher workstation 128 displays the location of security personnel who are close (and closest) to the last known location of a handset that is in an alarm state. Furthermore, the campus security management server 114 can be configured to automatically select a member of the security force and send a message to that member's handset to dispatch the member to the site of the emergency.

Sensor data can be selected by sensor type and displayed as an overlay on the campus map. A time sequence display of sensor data over a selected period of time allows the dispatcher to observe changes in these patterns. The time sequence data can be replayed, paused, rewound and fast forwarded, and the replay speed can be varied. Additional information about the dispatcher workstation 128 is provided above and below.

Stealth Mode

The handset 100 can be configured to recognize a "stealth code" that, when entered by a user, causes the handset to send a message to the campus security management server 114 indicating that communication with the user may increase the user's risk of harm. While in stealth mode, the handset 100 repeatedly sends its position information to the campus security management server 114, such as once per second. The campus security management server 114 displays information about the handset 100 on the dispatcher workstation 128, and security personnel are dispatched to the location of the user. Covert communications with the handset can continue, such as to obtain location information about the handset or sensor data.

When the user's handset has requested stealth mode, attempts to send messages or communicate with the user using text messages are disabled. Voice communications from the user's handset are not, however, disabled. An override capability is provided. Configuration options control if stealth mode can be overridden by the campus security management server 114 or the user.

Software in the handset 100 is configured to make the handset act and appear as though all monitoring has ended, e.g. the screen of the handset does not display an indication that the handset is being monitored, and the handset appears to respond normally to keystrokes on the keypad, although the handset remains in stealth mode. Once the handset 100 enters stealth mode, only security personnel can deactivate stealth mode via an exchange of messages between the handset and the campus security management server 114 or by manual entry of disable codes on the handset by security personnel.

If an attacker instructs the user to discontinue an automatic escort, the user can enter the stealth code instead of the discontinuance code. Since in stealth mode the external behavior of the handset (as visible to the attacker) is identical to the handset's behavior when monitoring is disabled, the attacker should not be aware that the handset continues to be monitored.

The handset 100 can be configured to display a user-configurable icon when the handset is in stealth mode and to display a different user-configurable icon when the discontinuance code has been entered into the handset. An attacker may be aware that the handset is capable of entering stealth mode, but the attacker is unlikely to be aware of the stealth mode icon or the icon that indicates that the discontinuance code has been entered. Thus, the attacker cannot tell which state the handset 100 is in. Any subsequent attempts to enable or disable monitoring appear to operate normally.

When the handset is in stealth mode, displays, such as progress bars and other indications of monitoring activity, are suppressed. When in stealth mode, all necessary handset behaviors are altered to make the stealth code appear to be the deactivation code. Even attempts to enable monitoring appear to work, and the stealth code appears to act as a discontinuance code.

Stealth mode may activate additional features, as supported by the handset and configured in the user's profile, such as opening a one-directional voice channel to the campus security office (to audibly monitor the situation) and/or activating an image capture and transfer capability to transmit images from the handset to the campus security office.

In stealth mode, a call can be automatically placed to an emergency service (such as 911) and a pre-recorded message can be sent to that service. The message can identify the user and notify the emergency operator that the user is unable to speak with the operator and that the operator is requested not call back to the user. This feature can be employed if permitted by the emergency service. It is intended that the recorded message be produced by or in cooperation with the security services in order to ensure that the message meets all emergency service requirements. A system configuration option regulates whether this message can be created and/or altered without security services involvement. Different messages can be sent based on data available to the handset about the emergency, including biometric and environmental data.

Wearable Devices for Emergency Communication

As discussed above, sensors and wearable devices can communicate with the handset 100 over a wireless channel, such as Bluetooth. These devices can be configured to trigger emergency notifications via the handset, including placing calls to 911, placing calls to security services or triggering alarms. Some wearable devices are manufactured with unalterable and unique identification codes. A user can own one or more wearable devices. Each wearable devices should be tested and in the wearable devices identification code should be registered with a corresponding handset. This testing and identification code registration can be automatically controlled by the handset. The registration results in an association of the wearable devices to both the handset and the user's data record in the user information database 130. Once the wearable device is registered, the user can configure the handset to initiate calls and requests for assistance to a designated emergency service, such as 911 or campus security. This configuration information is also stored in the user information database 130.

While in test mode, the wearable device sets a test message flag in its emergency transmission message. If another handset receives the wearable device's signal while the device is in test mode, the receiving handset ignores the message, because the receiving handset detects the test flag.

The handset software recognizes and acts on all messages from wearable devices that are registered to that handset. On the other hand, if a handset receives a message from a device that is not registered to that handset, the handset and sending device are referred to as being "foreign," relative to each other. If a handset detects a message from a foreign device, the handset composes a new message that includes the received message and the identification of the sender. The receiving handset flags the message as being received from a foreign device:

The receiving handset also includes the receiving handset's location in the new message. Because of variations in handset and wearable device features and programming, interpreting the received message is not possible at the receiving handset. The receiving handset transmits the message to a campus security management server 114 using the handset's primary means of communication, thus acting as a relay station for the received message. The message contains a unique device identification code that was assigned by the manufacturer of the device. The code carries no user information, but it permits the campus security management server 114 to identify the handset that it was assigned to and subsequently all other data associated with that handset, including the user's data and the handset's configuration information from the user information database 130.

The wearable device includes a mechanism for explicit alarm activation. This mechanism requires an action by the wearer that is unlikely to occur accidentally, in order to reduce the likelihood of false alarms. While the exact mechanism varies by device, a bracelet or watchband may trigger an alarm if opened/removed while alarms are enabled. Some wearable devices may have a normal orientation and may trigger an alarm if they are placed in an unexpected orientation for more than a programmed period of time.

If a user activates the wearable device alarm and the handset subsequently loses contact with the wearable device, the handset notifies the campus security management server 114 of the loss of contact, including the position of the user's handset at the time the signal was lost.

The wearable device communicates with the handset using standard wireless interfaces, such as Bluetooth. This creates several additional opportunities for detection, including the ability for a security officer to locate the wearable device when in close proximity to the device and for distributed wireless networking stations to detect the device. The detection of the device can provide a crude tracking mechanism when the handset is no longer in the possession of the user. Any wireless networking node capable of communicating with the device can detect and report the presence of an activated wearable device. While the position information is not precise, a succession of detections can help direct security officers to the vicinity of the victim, possibly getting close enough to detect the signal directly using portable, and possibly directional, receivers.

The wearable device supports frequency and channel hopping on standard wireless interfaces and channels, so the wearable device can interoperate with a variety of makes and models of handsets. In addition, the user is also not required to set a particular interface operating frequency or channel, because configuration of the device is automatically managed by handset and system software. This flexibility provides the ability to support interface changes introduced or mandated by the handset manufacturers, as well as maintaining the ability to communicate with the handset while complying with any changes in operating requirements imposed by the carriers. The device utilizes a common message format and encryption schemes specified by handset manufacturers to maintain user security and interoperability with all makes and models of handsets that utilize these standard interfaces.

When placed in emergency transmit mode, the device transmits a complete message on its primary interface frequency or channel. The device then automatically initiates frequency and channel hopping to potentially take advantage of nearby handsets that may operate on other frequencies. The software running on each subscriber handset monitors its primary interface frequency or channel and detects any emergency broadcast, since it recognizes the message format as well as a potentially valid wearable device ID. This provides for the possibility of detection by other subscriber handsets that use different frequencies or channels, because they are in the physical proximity of a wearable device in emergency transmit mode.

When all supported frequencies or channels have been used for emergency transmission by the wearable device, it repeats the emergency message sequence by returning to its primary interface frequency or channel assignment and then continues transmitting. Transmission continues until the campus security management server 114 is able to communicate with the device on Bluetooth or another wireless interface or security personnel physically reset the device using the device manufacturer provided tools.

If the handset is separated from the wearable device, the wearable device continues to transmit a signal that can be detected over a short distance, and the handset issues an alarm, which includes position information. The alarm is transmitted to the campus security management server 114, which begins tracking the handset. The position of the handset (when it became separated from the wearable device) is reported to the campus security management server 114. Initially, it cannot be determined if the wearable device or the handset was separated from the user. The handset can be monitored and the position of the wearable device may be detected by other handsets.

If the user intentionally drops the wearable device or the device is knocked off in some way, the handset is likely to remain with the user. If the user drops the handset, the handset is unlikely to move. The security staff know to attempt to locate the wearable device, which is likely to remain with the user. If the handset is stolen from the user, the handset is likely to continues to move, but the user is in no further danger, so no alarm need be raised. If the user has multiple wearable devices, one may be dropped and another confirms that the handset is still with the user. If more than one wearable device loses contact with the handset, it is highly likely that the handset is not with the user, unless there has been a handset failure, in which case it is difficult to determine whether or not the user is in danger.

Wearable Device Activation

Due to the large number of erroneous 911 calls caused by pre-programmed 911 buttons on mobile handsets, handset manufacturers no longer include these buttons on handsets. Furthermore, legislation in some states now prohibits the use of autodialing devices to call 911. However, a wearable device button functions can be programmed to allow a user to quickly summon help in the event of a personal emergency, while minimizing the possibility of unintentionally generating a 911 or other type of emergency call. The wearable device must be activated from the handset using a programmed operation on the handset to which it is registered, which transmits an activation code to the wearable device before the alarm activation will work. The wearable device is also deactivated using a programmed operation on the handset.

Wearable Device Buttons

The primary function of a wearable device is for a user to be able to quickly summon help in the event of a personal emergency of a nature that prevents them from using their handset to make an emergency call. The wearable device can be equipped with recessed buttons, and the device can be programmed to recognize sequences of button pushes to generate an emergency call.

Depending on the type and geometry of the wearable device, one or more of the following activation mechanisms can be employed to call 911.

A two button device with sufficient space between the buttons to make it easier to press each button individually can be used to generate a call by using a two-button depression sequence. The user first presses, then releases, either button and then must press and release the other button within a maximum elapsed time.

In another embodiment, a third button is placed between the other two buttons. To activate the device, the user presses the two outside buttons without pressing the center button.

In yet another embodiment, a single button is depressed a predetermined number of times, such as four, within a maximum elapsed time to generate the call. Four button depressions is equivalent to the number of keystrokes a user would make to completely dial a 911 call using a handset. This mode could also be implemented using any one button on the two-button or the three-button device.

A call to the campus security management server 114 is not bound by 911 restrictions on autodialing. The wearable device can be programmed to call 911 in response to a button sequence, such as one of the sequences described above. The wearable device can also be programmed to call the campus security management server 114 or send a data message to the server if the wearable device detects a different button sequence or if the wearable device detects a potentially dangerous situation, such as the device is removed from the user without first disarming it, a body temperature sensor detects a temperature beyond a predetermined threshold or a pressure sensor or other device provides a positive indication of a separation of the wearable device from the user. A pre-recorded message can be played over the call, or data describing the situation, as discussed elsewhere, can be sent to the campus security management server 114.

Emergency Beacon

If a user is unsuccessful in placing a call to an emergency service (such as 911), and the beacon feature is enabled, the handset requests assistance from other (secondary) handsets in the area. The first secondary handset with available telephone service that responds initiates a 911 call and links the originating handset to the 911 call. As discussed above, several secondary handsets can link together in a daisy-chain, if necessary. Depending on what the 911 service permits and supports, the secondary handset(s) may serve as only an audio relay or it(they) may also relay data. The relayed data can include the fact that the call was relayed, the identity (e.g. phone number) and location of the originating handset and the relay path (if multiple handsets form a chain).

When a handset responds to an emergency beacon request and becomes part of the relay network, audible, visual and/or tactile (e.g. vibration) indications are produced on the secondary handset(s) to notify their user(s) of the secondary handset that the handset(s) is(are) in use supporting an emergency call. The user of each secondary handset is requested to remain stationary, if possible, to ensure that the connection remains stable. When the call ends, another signal is sent to notify all handsets that acted as relays that the handsets are no longer involved in an emergency relay and their users are free to move.

If a relay connection is lost, the originating handset attempts to place a 911 call. If that call fails, the handset again requests assistance from other handsets in the area.

A similar relay mechanism is provided to connect to campus security, should the normal communications path be interrupted, which could occur under some conditions, such as localized power failures. Since this is usually a digital network connection, rather than a telephony connection, extending the network simply requires the secondary handsets to act as limited routers. The limited routing function routes only messages that are destined to the campus security management server.

Secure Locations

Two types of locations are considered secure locations: a campus security facility and a user's "home" location. Campus security facility coordinates are captured when the system is initially configured. A system configuration option determines whether a user can program the home location or whether a security officer inside a security office must do this. The coordinates of any secure locations are stored at the campus security management server 114 and stored encrypted in the handset.

When a handset reports its position and a campus security management server 114 verifies it to be at a secure location, the secure functions of a handset can be programmed. The first such function that should be programmed is the user's security code. That code should be provided by the user when at a secure location in order to permit changing other secured features, such as alarm and stealth codes, configuration parameters that affect security functions and any other features that must be restricted to the user.

When away from a secure location, security option settings may be changed to be more restrictive and subsequently less restrictive, but generally not less restrictive than the last setting programmed while at a secure location.

Docked State

For portable handsets that have different personalities when located at "home" vs. away from "home", such as combination cellular and portable wireline telephones, the knowledge of the state of the device can be used to determine location when at "home." A similar location capability can be used when the handset is docked in a device having a fixed, permanent location. This "docking station" can provide additional features, including serving as a charging base for the handset and the wearable device(s) and a means to permit changing certain programmable features that cannot be changed when undocked.

Home State

The user can follow a programming sequence that causes the handset to set its current geographic location as "home" using its built-in navigation receiver or can program the "home" location from a secure location. Once this "home" location is programmed into the handset, this location is considered a secure location. Only the handset proximity to this actual location or at another secure location will permit the User to reprogram certain security functions of the handset, such as the user PIN for enabling position information.

Broadcast Notification

As part of the security function, the system provides for broadcast notification to all subscribers of security alerts, including weather alerts, natural disaster warnings (e.g. earthquakes), fire, bomb threats, terrorist threats, reported assaults or other potentially dangerous situations. Some warnings may define a region within which there is a hazard. The handset conveys the message and produces audible, visible and tactile (e.g. vibrating) warnings that the user has just entered the region where there is a known or suspected hazard.

Hazard Probes

When a sensor alarm indicates a risk that may affect multiple people in a region, the campus security management server 114 sends a message containing a set of coordinates that define a region and indicating a type of sensor of interest. All handsets that find that they are within the specified region and that have the indicated type of sensor report their sensor data to the campus security management server 114. These reports do not necessarily identify the sender, and they report sensor values, whether the values indicate a hazard or not.

Other Monitoring

A campus security organization may temporarily issue handsets and wearable devices to visitors, such as vendors and maintenance technicians. The devices can provide services ranging from identification and access control to monitoring and recording the places where the visitors travel on the campus. The wearable device and handset can be configured such that separating the wearable device from the handset or removing the wearable device trigger an alarm. Deviating from allowed locations causes the handset to issue a warning to the visitor and, if the visitor does not return to an allowed area, to issue an alarm. The visitor's location is reported to the campus security management server 114 frequently, and a log of where the person traveled is maintained by the server. The warnings can also help guide the visitor. A wrong turn can result in a warning, thereby guiding the person to the proper destination. Visitor authorization is typically programmed to expire at a certain time. If the visitor is present on campus near the expiration time, the handset produces a warning to the visitor. If the visitor remains on campus beyond the expiration time, an alarm is triggered. If the visitor attempts to leave campus with the handset, i.e. if the visitor's trajectory is not consistent with a return to the visitor center or security office, an alarm is generated. If the visitor attempts to disable the handset or wearable device, an alarm is generated.

Foreign Campuses

A substantial number of users visit other campuses for extended periods of time to attend classes, meetings or services. The user can reconfigure his or her handset to communicate with a campus security management server other than the server on the user's home campus. The user can effect this reconfiguration by visiting the host campus security management server's web site, directly registering with the host campus security management server or by commanding the handset to automatically register upon arrival at the host campus. The user information database 130 remains on the user's home campus security management server. Portions of the user's subscriber information, including wearable device and handset information, are copied to the host campus security management server. Automated registration occurs if a handset determines that its location is outside its home campus or if the handset contacts its home campus security management server and that server determines that the handset is located within a region managed by another campus security management server. Each campus security management server provides routing services to other campus security management servers, so contact with the home campus security management server is supported on host campuses. The automated registration system is typically used for short-term visits to other campuses, such as sporting events. Manually changing registration is more typically used when a longer-term change in default campus security management server is desired.

When an alarm is generated while on a host campus equipped with a campus security management server, an emergency message is sent to the subscriber's home campus security management server. The home campus security management server determines that the event is occurring within a control region of the campus being visited and forwards the emergency message to the appropriate host campus security management server. All subscriber information, other than that previously designated as nontransferable, is forwarded to the host campus security management server.

If a subscriber generates an emergency event that is outside the control region of any campus security management server (e.g. off campus, but within communications range), the transmitted emergency message and all subsequent messages are automatically logged in the subscriber database by the home campus security management server. The Security Management System campus security management server can be configured to flag these messages for administrative review and/or to produce an operator message or alarm.

Lost Handset Locator

If a handset 100 is reported lost and the user authorizes remote activation, the campus security management server 114 can activate the handset and determine its location. The user selects a code, similar to a personal identification number (PIN) used for ATMs, which permits security personnel to remotely activate handset monitoring. This number is not known and is not available to security personnel, preventing security personnel from remotely activating monitoring without a user's permission and knowledge. A user can override this safeguard by altering a user profile setting that cannot be altered by security personnel.

Remote Handset Lockout

Many handsets employ various types of keypad lockout mechanisms. Currently, these lockout mechanisms can be invoked only from the handset keypad. The software in the handset 100 provides a handset keypad emulation function to emulate the keypad sequence used to disable the keypad, as if the user had done so from the keypad. If the user misplaces or otherwise loses control of handset 100, and the user does not want to permanently disable the handset by notifying the handset carrier, the user can request the security organization to prevent use of the handset by issuing a remote keypad disable command. The user notifies the security organization that the user wishes to lockout the handset keypad and provides the security organization with the user's authorization code to activate this function. A security officer issues the remote keypad disable command on the dispatcher workstation 128, and the campus security management server 114 send a command to the handset 100 to invoke the keypad emulation software.

In one embodiment, if the handset 100 becomes separated from the wearable device 121 when the wearable device is active, the software in the handset automatically deactivates the keypad and notifies the campus security management server 114. Thus, to re-activate the handset keypad, the handset must still be in the user's possession or in the possession of a person who knows the user's security code.

Use of Other Handset Features

Other features commonly available on other platforms, such as wireless PC and PDAs, that could serve as the handset include audio streaming and image capture. Embodiments of the campus security management server 114 can remotely enable these features when an alarm has been triggered, thereby enabling the gathering of additional data. Images may provide visual clues that help pinpoint a location of the handset, provide a picture of an attacker or information about the situation, including the number of assailants, if weapons are involved, if the victim has been injured and in what way. Audible information can include conversations, identifiable voices and additional information about the level of danger the user is facing.

Discovery and Registration

Several methods of discovery by the campus security management server 114 of the presence of registered handsets are possible. Generally, discovery occurs as a result of periodic broadcast messages sent by the campus security management server 114 that request a registration. If a handset 100 receives such a message and is not current registered, or the handset receives a message from a campus other than the one where it is currently registered, the handset 100 registers with the requesting campus security management server.

If the handset 100 is registered with one campus security management server and receives a request for check-in from another campus security management server, the handset attempts to contact the first campus security management server. If the handset 100 cannot contact the first campus security management server (i.e. the handset has lost the connection), the handset attempts to register in with the other campus security management server. The second campus security management server forwards the registration request to the handset's home campus security management server for validation. The user's configuration (stored in the home user information database 130), the home campus security management server's configuration and the other campus security management server's configuration control whether the handset 100 is permitted to register with the second campus security management server.

When a handset registers with a campus security management server, the telephone number of the associated security facility is provided to the handset and is used as the active security facility.

User and Handset Registration

Various types of user and handset registrations are provided to support different needs. Often, the owner of a handset may differ from the user. For example, a handset may be registered to a parent of a student or to a business. When a multiple-user handset is registered with the security management server, each user is assigned a unique identification code by the security management server. On completion of the registration and software initialization of the handset, the server then loads all user identification codes into the handset. Any registered handset user can then enter his or her unique identification code, which "locks" that user to that handset until another registered user enters their code, thereby "locking" that handset to the new user.

Registrations are configured to expire at various times, depending on expected periods of validity. Permanent employees can be registered without expiration. Students can be registered for a semester. Temporary users can be registered for a day. Temporary registrations generally provide little information and can be completed very quickly. They provide less data about the user, primarily providing identification and affiliation. However, additional data, such as purpose and location restrictions, may be entered at the time of registration. For vendors with frequent presence on campus, a registration can be created and stored, then called up a given a short-term lease (e.g. for a few hours or days).

User and Handset Deletion

In general, there is no need to delete users, except when one is created erroneously or when the local administration deems it beneficial to reduce the database size or eliminate stale data. When deleted, the user is initially flagged as marked for deletion and the operator can provide a reason for deletion. Prior to actual removal from the database, the system requires that a system archive be created with the user marked for deletion and containing any reasons provided.

User Configuration and Testing

Users can modify some configuration options and can test critical functions to ensure that the handset 100 and wearable device(s) 121 are operating properly. Most configuration changes and some testing are only permitted when the handset is located at a security facility or at that user's designated "home" location. When a user lives off-campus, a local location, such as an office, may be designated as the home location. Setting of the home location is typically done during initial setup and prior to normal operation.

Configuration changes that increase handset security settings may be performed when away from home, but changes that would decrease handset security settings below the last setting done at home or changes to security codes are not permitted when away from home.

Test functions are provided that allow a user to verify most functions, including the ability to connect with the campus security management server 114, operation of position determining functions, check access codes and test wearable device communications. Checking of access codes is permitted only at the home location, while verification of communications, positioning support and wearable device operation are possible at any time. For example, the tests for communications between the handset and wearable devices report either that a failure was detected or no failure was detected. No indication is provided as to whether such devices exist or how many there are.

To begin a test, the user selects a test mode on the handset and is presented with a list of options that depend on the user's location and the configured options. If the handset is unable to determine its location, it assumes that it is not at home. All options are presented when the handset 100 is at home, but a more restricted list of options that do not reveal security information is presented when the handset is not at home.

Handset Data Archive

The handset can collect all stored data, including routes, contact information, directories, options, etc., tag it with a version, compress it, encrypt it and upload it to the user database 130, which stores the data on behalf of the user. The user is able to retrieve the archived data and download it to a user's new handset.

Campus Security Management Server

The campus security management server 114 is the central data repository, registration station, coordination station, display station and primary security officer interface to the system. It receives all emergency notifications, monitoring requests and position reports. It provides the security officer with the visual and audio interactive capabilities. Every report or action involving the campus security management server 114 is logged and time stamped. Key attributes, such as type of action or report, location, value reported, etc. are logged.

When a member of the security organization logs into a campus security management server 114 via the dispatcher workstation 128, the access rights, display format and options programmed for that person are used to initialize the operation. The system logs (stores) when the person logs into and out of the workstation 128.

The key components of the user interface are the map window(s), route selection window, user data window(s) and dispatcher window. The map windows show campus features and handsets being monitored. The map views can be zoomed in for more detail or out for a wider perspective. Displays of trajectories of non-emergency monitored handsets can be disabled and displays of emergency trajectories can be moved to separate map windows. Various overlays are available that can be enabled or disabled, including security personnel and visitors. The route selection window provides a static map of the campus with location designations and provides a lookup capability by address, building name, building/room number and key terms. A route selection map has available overlays for signal coverage, lighting, security patrol routes, path status (such as snow plowing) and temporary changes, such as construction. The user data window is enabled for emergency monitoring only, and only with appropriate privileges. The dispatcher window provides controls for interactions with users and security staff.

Architecture

One or more peer servers contain user data, the GIS database 132 and connections to the location assistance (GPS/WAAS) receivers 122. Users are primarily associated with one campus security management server 114, but can have one or more designated backup campus security management servers. When multiple campus security management servers are available, each server has a primary set of users, but the server can be configured to act as a backup server for other users. Each server provides local storage redundancy and may provide remote or alternate site redundancy as well.

One or more dispatcher workstations 128 serve as workstations for security personnel. They provide administrative support for registering new users, changing options that require security assistance, communications capabilities, information display and route selection. Three levels of access are enforced: security administrator, security officer and dispatcher. The security administrator level has all privileges, including the privilege to change security system settings. The security officer level has most privileges, including access to user data when an alarm has occurred. The dispatcher level allows only route selection support and routine monitoring. Security administrator privileges are not provided to system administrators by default. It is necessary to assign a primary security administrator when the software is first installed and only a security administrator is permitted to change campus security management server access levels.

The dispatcher workstations 128 may be configured to provide full redundancy or separation of responsibilities. For example, certain regions can be handled at each workstation 128 or alarms may be handled at different workstations that do not handle other activities. One primary person is typically designated to handle any requests not specifically routed to a certain person or workstation 128. It is possible to divide work through one of several mechanisms, including an escalation mechanism, in which alarms are sent to a different workstation 128; a regional distribution, in which the current location of the user determines who handles the alarm; or through a supervisory assignment function, in which a user is assigned to an officer. The assignment function can be used to reassign responsibilities as well.

Dispatcher Workstation

The dispatcher workstation 128 is used when a user has requested monitoring or when the campus security management server 114 receives an alarm message. The positions reported by the handset are displayed on a map, showing the position of the handset at the time of the report and any relevant previous positions that are available. Maps can be zoomed in or out to show more detail or to show a full trajectory, planned route or more information about the environment, such as the current position of security officers. When regions, classes or groups of monitored routes are separated into multiple windows, the windows can be arranged on the display by dragging them, resizing, minimizing and maximizing them. The settings that are active are retained so that an officer can log out and restore a preferred screen layout at the next login. Trajectory-specific settings are not retained, since they are not likely to be appropriate when the officer logs in again, but any settings and arrangement related to regions and groups is stored.

While being monitored, the campus security management server 114 collects, retains and displays all position reports.

In the case of an alarm, any previous positions recorded by the handset 100 is transmitted and the campus security management server 114 displays any information that is less than ten minutes old. Older reports that were previously provided are retained and can be displayed upon request.

Figure 8:
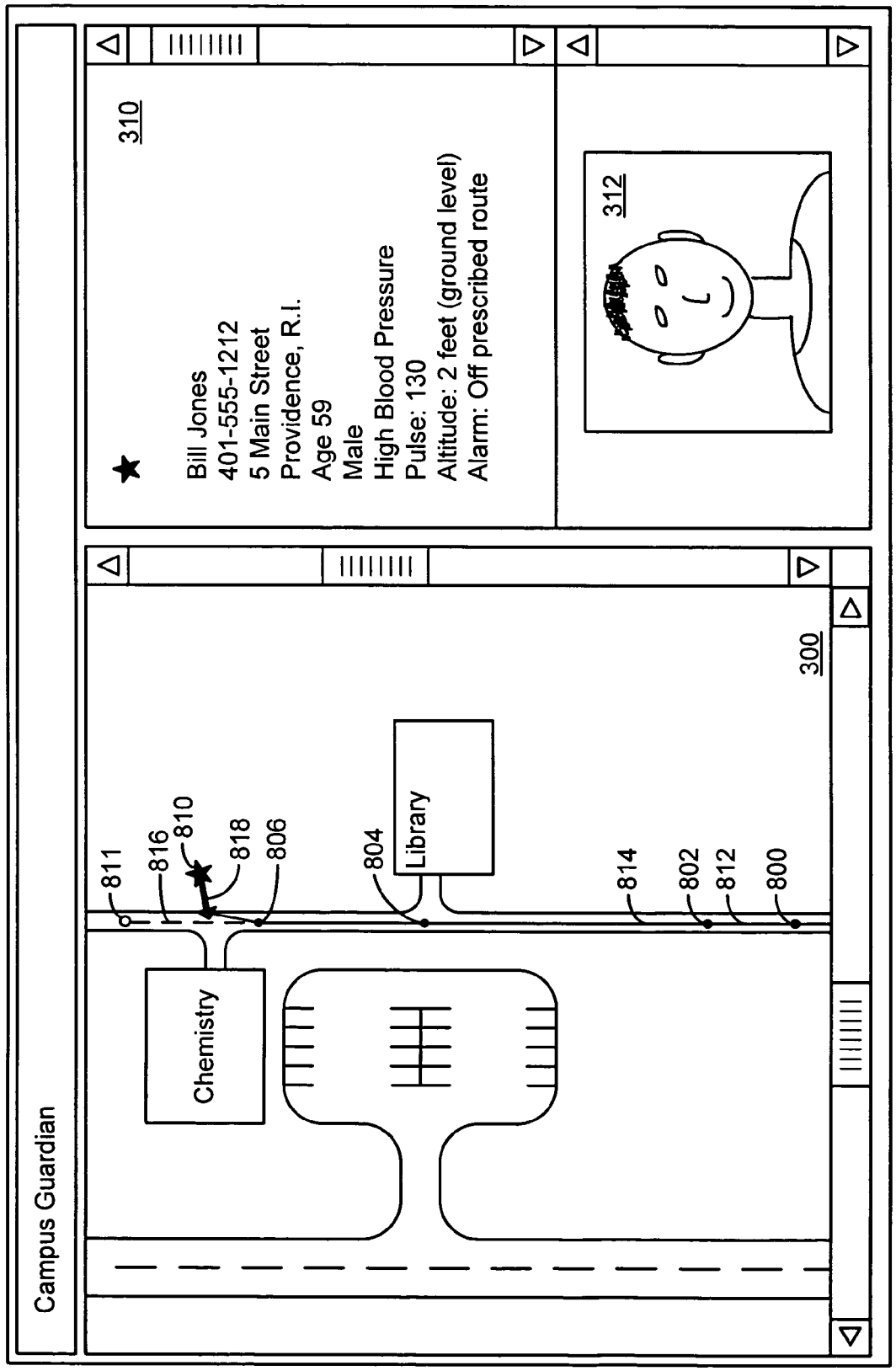
FIG. 8 is another exemplary display shown on the dispatcher workstation of FIG. 1.

In either case, individual reports are shown as small geometric shapes (such as circles, squares, triangles and a star) and are connected by lines. An exemplary display is shown in FIG. 8. A square designates a starting point (or the oldest available historical data) and an ending point for monitoring. A circle designates an intermediate report (without a change in direction) or a first displayed report of historical alarm data (when more reports are available, but none is displayed). For example, circles 800, 802, 804 and 806 represent reported (checked-in) locations for a user. A triangle, such as triangle 808, designates a point where a change in direction occurs. A star, such as star 810, designates the latest reported position for a handset 100. The entire planned route is displayed when monitoring, with past reports shown as filled shapes, such as circles 800–806, and future expected reports shown as open (unfilled) shapes, such as circle 811.

The lines connecting the shapes vary in style and color to convey additional information. Different colors are used for each trajectory displayed on one screen. Solid lines, such as lines 812 and 814, are used for historical data and dotted lines, such as line 816, are used for future segments of planned routes. An emergency trajectory (a path followed by a user for whom an alarm is active) is bold, as show for line 818. Such a line is green for points prior to the alarm, yellow at the point of the alarm and continuing to the last reported position and red at the last reported position. Any overdue report is red and flashing. As with non-emergency monitoring, historical shapes and lines are filled and solid, while planned future points are open and dotted. A semi-transparent overlay is available showing signal coverage in order to help the security officer assess the likelihood of a missed update due to signal loss.

The campus security management server 114 provides several data display management capabilities to assist in managing trajectory monitoring. Monitored trajectories may be clustered by map region selection or by manually selecting trajectories to group on a display. This is especially useful in order to maximize map detail and assist in isolating individual trajectories, which is easier when displaying a smaller area. A map window can be opened and a trajectory can be dragged into the window, displaying a map region that contains the trajectory and the selected destination. This can be used to either group trajectories or to provide a map window for a single trajectory.

Positioning the mouse over a point causes the position (description) and time of a report to be displayed. Clicking on any part of the displayed trajectory when an alarm is active and with the appropriate privileges results in a display of the user data in a separate window. A button is provided that allows a trajectory to be moved into a separate map window and an option is provided to cause a separate map window to be opened automatically when an alarm is generated. When a map window displays an active alarm, changing the focus of the display to that window automatically places the user data in the data window. This ensures that the user data window is always consistent with the trajectory that is in focus.

Positioning the cursor over any active trajectory or point causes the system to display a summary data table for a few seconds. Right licking on any active trajectory or point provides a list of options from which the summary data can be selected. In this case, the window is movable and remains present until closed with a line connecting to the last reported position of the associated user. This window includes the name, status, closest labeled location, grid location, height relative to ground level and floor, if appropriate.

In most cases, a windowed display is adequate to manage the user population. However, in some installations, such as those with large user populations and large campus areas, it may be desirable to set up multiple-display workstations that allow for large area displays, close up map displays, separate user data displays, etc. The campus security management server 114 supports a desktop metaphor and can be used with display capabilities ranging from single-monitor displays, through multiple-monitor displays to large display walls.

At any time a monitored user's trajectory goes beyond a map window, the display is either shifted or rescaled to bring the new point into the display. If the display can be shifted without losing any data points from the last ten minutes of any trajectories in that window, the display image is moved. Otherwise, the display locates the trajectory that is most likely to reach an edge of the display next, based on the amount of movement between the last two reports. The image is rescaled to provide at least enough space at each edge to accommodate one more sample with the same interval size.

A legend is automatically generated for any elements that are currently active (e.g. routes, signal coverage, etc.), including icons, line colors and shading colors.

Security Officer Display

Security officers' positions can be displayed overlaid on the screen or can be suppressed. Any officer that has been dispatched to a user is shown in this window in color, while other security officers are shown in gray. Officers not involved with this user may be suppressed by clicking on an on-screen button. The trajectory for the dispatched officer can be shown along with the trajectory of the user and an approximate time to intercept. This trajectory display can be made less significant in order to see the user trajectory more clearly, by displaying the trajectory as a series of dots representing position reports.

A security officer can be selected and dispatched to assist the user simply by clicking on the security officer's icon. This opens a communication channel to dispatch the officer. It also pops up information about the officer, including identity, rank, type of vehicle or other information that the security office deems significant.

Action List

When a request for monitoring or an alarm is received at the campus security management server 114, a list of actions is displayed as a checklist. The checklist is customized based on data provided by the user and/or the handset 100 and data stored in the user information database 130 and/or the GIS database 132, as well as data from other parts of the system. In addition, other actions are provided in a list that the security officer or dispatcher may choose from to augment the automatically generated list, based on information that is provided verbally or in some other manner. Some items are shown and checked off. For example, if the security office is being notified of a call that was placed to an emergency service (such as 911), "Notify public safety agencies" is listed and checked off.

If multiple officers are participating in handling the event, multiple dispatcher workstations 128 may be in use. All displays related to a single event are automatically kept consistent.

User Data Window

When a user data window is available, several push buttons are available in the window, including configurable buttons for customizing an installation. Among them are buttons to call the user, request an image from the user's handset 100 or a device communicably linked to the handset, show the planned route, show security officers' positions or notify police or an ambulance. A mute button is provided to allow audio monitoring while suppressing extraneous noise from the security center.

Displays are prioritized so that a new alarm causes a trajectory to be highlighted. Map windows are, by default, set to separate trajectory displays into three categories: monitored, warnings and alarms. A button is provided to combine or separate these classes of trajectories. When separated, any update to a higher priority (e.g. from warning to alarm) causes the window containing the upgraded trajectory to be maximized and moved in front of any lower priority window(s), and the window border is made to flash. Any position update in a window with an active alarm causes the window to move to in front of other windows.

Campus Map

The campus map data are uploaded from field data collection and from existing GIS databases (such as GIS database 132) to populate the basic infrastructure database, including labels, where available. A labeling function is also provided to display the campus map with each mapped location without a label highlighted in turn with a request for the operator to enter a label description. This allows physical locations of all primary designated points to be labeled. The primary designated points are those that represent permanent, recognizable points of demarcation, including intersections of roads and walkways, rooms in buildings, entry points into buildings, gathering points such as bus stops, event venues, stores, cafeterias, etc. There are two types of designations: points and regions. Point designations have coordinates and limits. Limits are specified as a horizontal radius and a vertical height, defining a cylinder. Regions consist of a list of points or a list of regions. The points can be designated as boundary points, such as by using a radius of 0, to define a contained region can or can be used to define a region as a series of points with non-zero radii. Boundary points are used to define large areas or areas that are difficult to map with one or more cylindrical point designations, while a sequence of cylindrical point designations can more easily map a curved walkway. A smoothing function automatically smoothes the edges of a region defined by a sequence of cylinders.

Secondary points or regions are used to further qualify defined regions. For example, secondary points can define a "west sector of an open area" or a "back of the store." They "belong to" (are associated with) a region, so they have a region identifier in addition to the attributes of a point or region. For purposes of meaningful designations, regions can also be composed of a list of regions. This permits the number of points that define a simple region to be bounded and keeps the definitions of these regions manageable, but it permits compound regions of arbitrary complexity. A simple region can be tagged as a member region, so it is not given a label and is not used as a destination, avoiding cluttering of maps and lists.

When selecting a region, a larger region that contains a region of interest may be specified. After a region is selected, a list of contained regions may be requested. This can be helpful, because one of the entries in the list of contained regions might suggest a more specific region of interest to select.

Signal Coverage Map

Signal coverage is mapped when coordinates are mapped. Coverage mapping includes identification of all signals employed by the system, including GPS satellite visibility, WAAS satellite visibility, cell tower reception, wireless LAN router visibility, Bluetooth availability, etc.

While field strength metering can be performed and atmospheric conditions can be factored in, generally there is only a need to designate field strength at a point as one of three qualities: reliable, unreliable or absent. If actual measurements are taken, intervening points can be estimated using linear interpolation. Despite inaccuracies inherent in this approach, it provides adequate accuracy for the intended purpose. When signals are simply recorded on the three-step scale, any point surrounded by reliable points can be declared reliable. Any point that is bounded on at least one side by a point having a reliable signal and bounded by at least one other point having an unreliable or absent signal can be considered unreliable. Any point surrounded by points having unreliable signals or bounded by a combination of unreliable and absent points can be considered unreliable. Any point surrounded by points having absent signals can be considered absent. It is desirable to provide a sufficiently dense sampling to make this algorithm effective. Generally, samples every 500 feet are desired, but samples every 1000 feet in each direction are adequate. If samples are less dense, a weighted average algorithm can be used based on the distance to each sample point and a score of 0 for absent, 1 for unreliable and 2 for reliable. The result is based on rounding, with 0.0–0.5 interpreted as absent, between 0.5 and 1.5 as unreliable and above 1.5 as reliable.

An approximate coverage map for each transmitter, when available, is used to assist in rapidly projecting the likely impact of loss of a transmitter. Using radial distances specific to each type of transmitter as approximations of coverage for each transmitter, the outer 10% of the radius defines the portion of the coverage area considered unreliable, with the inner 90% of the radius assumed to define a reliable region. This algorithm can be used to calculate an initial condition within the area affected by a transmitter that is known to have gone down. Actual communication from handsets can be used to correct this data over time. If a communication is received from a point that is currently characterized as absent, the point is recharacterized as unreliable. If a second communication is received from the point, the point is recharacterized as reliable. After each characterization update, the averaging algorithm discussed above is applied for points from which no calls have been received.

Illumination Map

At each point, a designation may be flagged as an illumination source. Data about the types of light fixtures and their illumination models can be stored in the GIS database 132. The models can come from vendor data or from field mapping of the boundaries of constant illumination. Regions of illumination can be defined to account for obstructions that cause irregular illumination.

Temporary loss of illumination can be logged via the campus security management server 114 when a security officer is notified that an illumination source is not operational. Since the map consists of individual point and pattern data, the map can be recalculated immediately. When notified that the problem has been resolved, this temporary outage can be removed from the system. Periodically, based on a period entered when the outage is recorded or at subsequent reconfirmation, a security officer is presented with data about the outage and asked to reconfirm that it is still out.

Foliage Map

A foliage map contains information about ground vegetation and trees and can be used to select routes. The information can indicate regions where satellite signals are obscured, lighting is shaded or attackers can hide. This information can also be used to estimate signal strengths from satellite, wireless carrier, WLAN and other wireless networks. The map can be based on photogrammetric data and can be updated occasionally as plants grow, die or landscaping is changed. Optionally, the system can estimate growth rates for plants.

Temporary Changes to Infrastructure

Temporary changes in infrastructure, such as construction, can be identified using the normal position mapping capability to identify the boundaries of a blocked area. This is taken into account when planning routes. Users who wish to dictate their routes can be informed about an obstacle.

Temporary Blockages

Temporary changes in route availability due to weather, accidents, crowds or special events may require that these routes remain unused by users. When the blockages are created on the security display, an expiration time is associated with each blocking feature. When the time expires, the operator is notified and can renew or confirm cancellation of the temporary route blockage. If the blockage is planned, the blockage can be scheduled in advance. A starting time is provided and the blockage is assumed to be present at that time and until expiration is confirmed. Any route that passes through a blocked location at or after the starting time should avoid including that region in the proposed route, even if the route begins before the blockage begins.

Temporary blockages are sometimes identifiable from late reports (i.e., handsets not arriving at check-in boxes before the respective due time windows expire). When a user's check-in report is late and the location reported is not the next expected point, it is possible that the user has taken a detour to avoid a temporary and undocumented blockage. If the user returns to the planned route, this becomes more likely. If a second user apparently detours in the same area, a temporary blockage is added to the routing database, along with an expiration time of 30 minutes. In the meantime, security personnel can confirm or reject the hypothesis, or a voice communication with a user can confirm or reject the hypothetical blockage. If the hypothesis is confirmed, the expiration time can be extended. On the other hand, if the hypothesis is disproved, the blockage can be removed from the GIS database 132.

Semi-Automated Route Monitoring

When it has been determined that the handset 100 is unable to provide location information, possibly due to a handset or wireless network malfunction, the user may request an in-person security escort, if available, or a semi-automated monitoring service. Semi-automated monitoring utilizes occasional calls or messages exchanged between the user and the security organization to verify that the user is progressing toward the destination and not in danger. Semi-automated monitoring relies on route selection and an agreement between the user and the security organization on call-in points. Typically, fewer call-in points are used in semi-automated monitoring than check-in points would be used in automatic monitoring of identical routes.

The security officer enters information about the call-in points into the dispatcher workstation 128, and the campus security management server 114 calculates estimated arrival times at the respective call-in points and stores call-in due time windows in the same way the server calculates check-in due time windows. The security officer expects the user to follow the prescribed route and call in upon reaching the call-in points. Each time the user calls in, the security officer manually enters data via the dispatcher workstation 128 to update the user's travel status. The normal late update alarms are in effect. Depending on the type of system deficiency, the campus security management server 114 may be able to send reminder messages as responses to a late call-ins. If so, the reminder messages prompt the user through audible or tactile announcements.

Late Report Alarm

If the campus security management server 114 does not receive a check-in by the end of its due time window, the server consults its database of signal coverage and determines if the likely explanation is loss of signal. If it determines that the signal is known to be weak in the check-in box and that there is no backup wireless infrastructure that should have been used by the handset to send the check-in message, the state of the user is upgraded to warning, but an alarm is not yet generated. An additional timeout period is established, based on the planned trajectory and signal coverage maps, but the additional period is not later than the next expected check-in due time.

The security officer can utilize several methods to automatically connect with the user in order to attempt to determine if there may be a problem. The monitor need only position the cursor over that user trajectory on the monitor display and select "Call Default" to place a call using the connection method tagged as most reliable. Alternatively, the security officer can select "Call" to provide a list of available communications channels.

If the user fails to answer the handset, the security officer can send a high priority message to the handset informing the user that voice communication with the security organization is required. The campus security management server 114 attempts to use multiple communications networks if the primary communications network connection does not result in a connection.

In the event that the security officer is unable to contact the user and cannot verify the status of the user's handset, the security officer can elect to dispatch a security officer to the known site or last known location of the user in order to determine if there is a problem.

Wireless Network Malfunctions

The loss of a communications site (e.g. cell tower) can result in a significant change in coverage. The outage can lead to false warnings and alarms, because the coverage data may not be accurate during the outage. By detecting such situations and informing the security staff of the approximate impact, appropriate changes can be made in response to events in the affected area.

Multiple late check-in reports in an area may indicate such a situation. For example, if a report is late and it is found to be a delayed report of the intended position plus an additional position along the correct route, it is likely there was a transmission failure at the missed point. Once verified, the operator can indicate each case, from which the campus security management server 114 can build an overlay indicating an area of temporarily compromised coverage. Additional techniques can be used to correct coverage data including sensor stations that detect loss of signal and arrangements with wireless carriers to report outages.

Temporary outages are maintained as separate overlays. If detailed mapping was not performed, these overlays may be only approximations. The overlay is built as a union of circular regions centered on points of missed reports after verifying that such events were not false alarms. An operator action is required to add a point to the outage map. A timeout is provided, after which the operators are reminded that the coverage outage needs to be reconfirmed or will be removed from the system.

Portable Campus Security Management Server

All functions available at the campus security management server 114 can be made available to mobile stations in cars or even on portable computing devices through a proxy capability. Most mobile stations support only a subset of the capabilities of a campus security management server due to limitations of the mobile device. Each time the capability it is deployed, it is explicitly enabled (and thereafter periodically or occasionally re-enabled) from a central campus security management server 114. If the capability is not re-enabled within a timeout period, the capability is automatically disabled by the campus security management server 114. A warning message is issued at the central campus security management server 114 a predetermined amount of time before a mobile station is automatically deactivated. If the station's lease is not extended within a station-specific time period, it is disabled. All mobile campus security management servers are continuously monitored and a map of active mobile stations is maintained on all central campus security management servers.

Remote Campus Security Management Server

A remote, or alternate campus security management server, usually located at another campus, can connect to a local campus security management server 114 in order to provide support for users when they are on a remote campus. An authentication process is required for each user requesting remote campus access. Once authenticated, the remote campus security management server is capable of accessing user data stored on a home campus security management server. Information is provided to the remote campus security management server only when a monitoring request or validated alarm is relayed to the home campus security management server.

Compatibility

To facilitate integration with existing systems, both static and dynamic data import and export capabilities provide field mapping and type conversions so that existing data can be imported and data produced can be exported. GIS data can be imported and updated GIS data can be exported. Portions of the user information database 130 can be populated from data in existing employee and student databases to avoid multiple data entry. Alternatively, this user information can be fetched from the existing employee and student databases when it is needed, thereby avoiding storing duplicate information. Information gathered in the registration process that complements existing student records can be transferred to the employee and/or student databases. Dispatch and security management software can be made to operate cooperatively or can be integrated, since the system does not assume that it is a standalone master system, making all capabilities potentially encapsulated within another complementary application.

Active data can be available in a form that is accessible through standardized interfaces, including ODBC and serial data streams. These make it possible to tie into other applications and databases that support such interfaces and allow the use of existing applications for many common activities and use the campus security management server software directly and simultaneously, when required.

Data Recording and Analysis

Extensive logs are maintained. Every event that produces data, from registration and check-in to alarms and position information, is logged. Furthermore, any communication can be recorded and logged, depending on configuration settings. Every entry is time-stamped and tagged with originator information. Changes that affect system capabilities, such as loss of a cell site, are logged. Response times can be measured for alarms and all actions taken are recorded.

Reports provide information about who knew what and when, why information was not available (such as lack of handset support, disabled by user configuration, not requested by a user, as indicated by audio recording of a conversation between the user and a security officer). Various standard reports are provided showing the amount of activity by type, false alarm statistics, account activity, activity by time of day, etc.

Training

Features are built into the system to permit simulations and drills for training. By directing handsets to use a specified campus security management server 114, a drill can be set up even on a campus with an active system to train new staff. Simulated messages can be sent and a training database can be used. Live campus security management servers do not display or respond to handsets or regions that are identified as under test. A campus security management server 114 can be equipped to receive or exclude all normal active data in addition to test communications while acting as a testing station. Outgoing notifications can be initiated by the operator under test and produce a simulated response sufficient for testing that expected operator actions are taken.

Each testing action is logged separately from normal actions. An evaluation component is provided with a testing scenario, which also contains relative events that specify that a response is to occur following some event. The interval between the event and the response is measured and reported. A report is generated that compares actual behaviors with expected behaviors and reports on consistency or deviations from the programmed expected behaviors.

A handset and a server have been described as each including a processor controlled by instructions stored in a memory. Those skilled in the art should readily appreciate that instructions or programs defining the functions of the present invention can be delivered to a processor in many forms, including, but not limited to information permanently stored on non-writable storage media (e.g. read only memory devices within a computer such as ROM or CD-ROM disks readable by a computer I/O attachment) or information alterably stored on writable storage media (e.g. floppy disks and hard drives). In addition, while the invention may be embodied in software, the functions necessary to implement the invention may alternatively be embodied in part or in whole using firmware and/or hardware components such as Application Specific Integrated Circuits (ASICS) or other hardware or some combination of hardware, software and/or firmware components.

While the invention is described through the above-described exemplary embodiments, it will be understood by those of ordinary skill in the art that modifications to, and variations of, the illustrated embodiments can be made without departing from the inventive concepts disclosed herein. For example, although embodiments were described in relation to a handset monitoring the location and movements of the handset and comparing that information to set of rules, the handset can send the location information to the campus security management server, and the server can compare that information to the set of rules. Accordingly, the invention should not be viewed as limited, except by the scope and spirit of the appended claims.

What is claimed is:

1. A system for providing an indication of a possible emergency situation, comprising:
    a wireless communication device operable to place a call to at least one first predetermined destination over at least one first channel, to generate a data message that includes three-dimensional positioning location information about the wireless communication device, and to send the data message including the three-dimensional positioning location information to at least one second predetermined destination over at least one second channel if the wireless communication device attempts to place a call to the at least one first predetermined destination; and
    a monitoring station in communication with the wireless communication device, the monitoring station comprising the second predetermined destination, the monitoring station being operable to receive the data message sent by the wireless communication device over the at least one second channel, and, in response to receiving the data message, to display information pertaining to a user of the wireless communication device including an indication of the three-dimensional positioning location information.

2. A wireless handset, comprising:
    wireless communications apparatus operative to place an emergency call to at least one first predetermined destination over at least one first channel;
    first logic operable to detect an attempt to place an emergency call to the at least one first predetermined destination; and
    second logic operable, in response to detecting the attempt to place the emergency call, to perform at least one predetermined action other than placing the emergency call,
    wherein the at least one predetermined action includes sending a data message containing information pertaining to at least one of the wireless handset and a user of the wireless handset to at least one second predetermined destination over at least one second channel.

3. The wireless handset of claim 2, wherein the first logic is operable to detect an attempt to place a telephone call to a predetermined number.

4. The wireless handset of claim 2, wherein the first logic is operable to detect an attempt to place a telephone call to 911.

5. The wireless handset of claim 2, wherein, to detect the attempt to place the emergency call, the first logic is operable to detect an attempt to send a data message to a predetermined address.

6. The wireless handset of claim 2, wherein the predetermined action comprises sending information about the emergency call attempt to the at least one second predetermined destination.

7. The wireless handset of claim 6, wherein the information includes the at least one first predetermined destination to which the emergency call was attempted.

8. The wireless handset of claim 6, wherein the information includes a current status of the emergency call.

9. The wireless handset of claim 6, wherein the information indicates if the emergency call was successfully connected.

10. The wireless handset of claim 6, wherein the information indicates a time at which the emergency call was attempted.

11. The wireless handset of claim 6, wherein
    the first logic is operable to detect the attempt to place the emergency call over the at least one first channel, the at least one first channel comprising a wireless link; and
    the information is sent via the at least one second channel, the at least one second channel comprising a data bearer channel of the wireless link.

12. The wireless handset of claim 6, wherein
    the first logic is operable to detect the attempt to place the emergency call over the at least one first channel, the at least one first channel comprising a first wireless link; and
    the information is sent via the at least one second channel, the at least one second channel comprising a second wireless link different than the first wireless link.

13. The wireless handset of claim 12, wherein the second wireless link comprises a wireless local area network link.

14. The wireless handset of claim 12, wherein the second wireless link comprises a Bluetooth link.

15. The wireless handset of claim 12, further comprising:
    a second wireless handset; wherein:
    the second wireless link comprises a wireless link to the second wireless handset, and the second wireless handset is operable to relay the information.

16. The wireless handset of claim 6, wherein:
    the first logic is operable to detect the attempt to place the emergency call over the at least one first channel, the at least one first channel comprising a wireless link; and
    the second logic is operable to test for accessibility of each of a plurality of wireless networks and to send the information over the at least one second channel, the at least one second channel comprising an accessible at least one of the plurality of wireless networks.

17. The wireless handset of claim 16, wherein the plurality of. wireless networks includes a wireless local area network and a common carrier wireless communication network.

18. The wireless handset of claim 6, further comprising:
at least one sensor operable to detect at least one physical condition proximate to the wireless handset; and wherein:
the information includes data from the at least one sensor.

19. The wireless handset of claim 18, wherein the sensor is operable to detect ambient temperature.

20. The wireless handset of claim 18, wherein the sensor is operable to detect smoke.

21. The wireless handset of claim 18, wherein the sensor is operable to detect oxygen level.

22. The wireless handset of claim 18, wherein the sensor is operable to detect at least one chemical.

23. The wireless handset of claim 18, wherein the sensor is operable to detect acceleration.

24. The wireless handset of claim 18, wherein the sensor is operable to detect sound.

25. The wireless handset of claim 18, wherein the sensor is operable to detect a heart rate of a user of the wireless handset.

26. The wireless handset of claim 18, wherein the sensor is operable to detect a body temperature of a user of the wireless handset.

27. The wireless handset of claim 18, wherein the sensor is operable to detect a blood pressure of a user of the wireless handset.

28. The wireless handset of claim 18, wherein the sensor is operable to detect a galvanic skin response of a user of the wireless handset.

29. The wireless handset of claim 18, wherein the sensor is operable to detect a respiration rate of a user of the wireldss handset.

30. The wireless handset of claim 18, further comprising:
a positioning system; and wherein:
the predetermined action further comprises sending three-dimensional location information about the wireless handset to the at least one second predetermined destination.

31. The wireless handset of claim 2, wherein the predetermined action comprises sending information about the emergency call attempt to the at least one second predetermined destination after the emergency call ends.

32. The wireless handset of claim 2, wherein the predetermined action comprises placing a second telephone call to the at least one second predetermined destination after the emergency call ends.

33. The wireless handset of claim 32, wherein the predetermined action further comprises sending information about the emergency call attempt via the second telephone call.

34. The wireless handset of claim 2, wherein the first logic comprises a speech recognizer coupled to a voice path of the emergency call and operable to recognize at least one of a predetermined plurality of words.

35. The wireless handset of claim 2, wherein the first logic comprises a recognizer coupled to a data path of the emergency call to monitor text sent via the emergency call and operable to recognize at least one of a predetermined plurality of words.

36. A system for providing an indication of a possible emergency situation, comprising:
at least one first wireless handset; and
at least one second wireless handset,
wherein the at least one first wireless handset is operative to place a call to at least one first predetermined destination over at least one first channel, to send a data message containing information pertaining to at least one of the first wireless handset and a user of the first wireless handset to at least one second predetermined destination over at least one second channel if an attempt is made to place a call to the at least one first predetermined destination, and, in the event an attempt to send a data message to the at least one second predetermined destination is unsuccessful, to send the data message to the at least one second wireless handset, and
wherein the at least one second wireless handset includes a relay unit, the relay unit being operable to receive the data message from the first wireless handset, and to relay the information to the at least one second predetermined destination via a wireless link.

37. The wireless handset of claim 36, wherein relay unit is operable to relay the information such that the relayed information includes an identification of the other wireless handset.

38. The wireless handset of claim 37, wherein relay unit is operable to relay the information such that the relayed information includes an identification of the wireless handset.

39. The wireless handset of claim 36, wherein the relay unit is operable to relay the information by placing a telephone call.

40. The wireless handset of claim 36, wherein the relay unit is operable to relay the information by sending at least one text message.

41. The wireless handset of claim 36, wherein the relay unit is operable to relay the information by relaying an audio signal received from the other wireless handset.

42. The wireless handset of claim 36, wherein the relay unit is operable to relay the information by sending the information over a wireless local area network.

43. The wireless handset of claim 36, wherein the relay unit is operable to relay the information by sending the information over the wireless link, the wireless link comprising a data bearer channel of a common carrier wireless communication network.

* * * * *

UNITED STATES PATENT AND TRADEMARK OFFICE
CERTIFICATE OF CORRECTION

PATENT NO. : 7,221,928 B2
APPLICATION NO. : 10/957083
DATED : May 22, 2007
INVENTOR(S) : Mark D. Laird et al.

It is certified that error appears in the above-identified patent and that said Letters Patent is hereby corrected as shown below:

Column 19, line 37, "location-deter ning" should read --location-determining--;

Column 43, line 66, "Right licking" should read --Right-clicking--; and

Column 46, line 7, "helpfiil" should read --helpful--.

Signed and Sealed this

Twenty-ninth Day of April, 2008

JON W. DUDAS
*Director of the United States Patent and Trademark Office*